(12) United States Patent
Dinsmoor et al.

(10) Patent No.: US 9,042,995 B2
(45) Date of Patent: May 26, 2015

(54) IMPLANTABLE MEDICAL DEVICES AND SYSTEMS HAVING POWER MANAGEMENT FOR RECHARGE SESSIONS

(75) Inventors: David A. Dinsmoor, St. Paul, MN (US); Joel A. Anderson, Brooklyn Park, MN (US); Timothy Denison, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 914 days.

(21) Appl. No.: 12/699,830

(22) Filed: Feb. 3, 2010

(65) Prior Publication Data

US 2011/0190853 A1    Aug. 4, 2011

(51) Int. Cl.
*A61N 1/378*    (2006.01)

(52) U.S. Cl.
CPC ...................................... *A61N 1/378* (2013.01)

(58) Field of Classification Search
USPC ...................................................... 607/60, 61
See application file for complete search history.

(56) References Cited

U.S. PATENT DOCUMENTS

| | | |
|---|---|---|
| 3,229,684 A | 1/1966 | Nagumo et al. |
| 3,758,865 A | 9/1973 | McKibben |
| 3,796,221 A | 3/1974 | Hagfors |
| 4,166,470 A | 9/1979 | Neumann |
| 4,197,850 A | 4/1980 | Schulman et al. |
| 4,345,604 A | 8/1982 | Renirie |
| 4,679,560 A | 7/1987 | Galbraith |
| 5,218,343 A | 6/1993 | Stobbe |
| 5,235,980 A | 8/1993 | Varrichio |
| 5,260,701 A | 11/1993 | Guern |
| 5,279,292 A | 1/1994 | Baumann |
| 5,314,457 A | 5/1994 | Jeutter |
| 5,324,315 A | 6/1994 | Grevious |
| 5,324,316 A | 6/1994 | Schulman et al. |
| 5,405,367 A | 4/1995 | Schulman et al. |
| 5,522,865 A | 6/1996 | Schulman et al. |
| 5,569,307 A | 10/1996 | Schulman |
| 5,630,836 A | 5/1997 | Prem et al. |
| 5,658,319 A | 8/1997 | Kroll |

(Continued)

FOREIGN PATENT DOCUMENTS

| | | |
|---|---|---|
| GB | 1492990 | 11/1977 |
| WO | 94/28560 | 9/1994 |
| WO | 2009/056167 | 7/2009 |

OTHER PUBLICATIONS

U.S. Appl. No. 12/699,822, filed Feb. 3, 2010.

(Continued)

*Primary Examiner* — Tammie K Heller
(74) *Attorney, Agent, or Firm* — Withers & Keys, LLC

(57) ABSTRACT

Implantable devices and related systems utilize power management features in conjunction with a recharge circuit that includes a coil and capacitance. The reactance such as the capacitance and/or inductance may be variable such that in the event of an overcharge condition, the reactance may be varied to change the resonant frequency of the circuit of the coil from the recharge frequency to another frequency to reduce the power being received. Other power management features may additionally or alternatively be employed. For instance, the device may send an uplink telemetry signal to an external device to request that recharge power be decreased. The device may switch additional resistance into the circuit of the coil to reduce the Q of the circuit. As another example, the device may clamp the circuit of the coil to ground.

22 Claims, 22 Drawing Sheets

(56) References Cited

U.S. PATENT DOCUMENTS

| | | | |
|---|---|---|---|
| 5,674,264 A | 10/1997 | Carter et al. |
| 5,680,134 A | 10/1997 | Tsui |
| 5,702,431 A | 12/1997 | Wang |
| 5,713,939 A | 2/1998 | Nedungadi et al. |
| 5,733,313 A | 3/1998 | Barreras, Sr. et al. |
| 5,741,316 A | 4/1998 | Chen et al. |
| 5,755,748 A | 5/1998 | Borza |
| 5,769,877 A | 6/1998 | Barreras, Sr. |
| 5,807,397 A | 9/1998 | Barreras |
| 5,814,089 A | 9/1998 | Stokes et al. |
| 5,945,810 A * | 8/1999 | Fujita et al. ............... 320/134 |
| 5,991,664 A | 11/1999 | Seligman |
| 5,995,874 A | 11/1999 | Borza |
| 5,999,857 A | 12/1999 | Weijand |
| 6,011,964 A | 1/2000 | Saitoh |
| 6,047,214 A | 4/2000 | Mueller |
| 6,185,460 B1 | 2/2001 | Thompson |
| 6,308,101 B1 | 10/2001 | Faltys |
| 6,321,067 B1 | 11/2001 | Suga |
| 6,442,434 B1 | 8/2002 | Zarinetchi |
| 6,456,833 B1 | 9/2002 | Sessink |
| 6,456,883 B1 | 9/2002 | Torgerson |
| 6,477,425 B1 | 11/2002 | Nowick |
| 6,516,227 B1 | 2/2003 | Meadows et al. |
| 6,549,807 B1 | 4/2003 | Kroll |
| 6,631,296 B1 | 10/2003 | Parramon et al. |
| 6,701,188 B2 | 3/2004 | Stroebel |
| 6,772,011 B2 | 8/2004 | Dolgin |
| 6,856,838 B2 | 2/2005 | Parramon et al. |
| 7,015,769 B2 | 3/2006 | Schulman |
| 7,079,901 B1 | 7/2006 | Loftin et al. |
| 7,107,103 B2 | 9/2006 | Schulman |
| 7,167,756 B1 | 1/2007 | Torgerson et al. |
| 7,177,691 B2 | 2/2007 | Meadows |
| 7,177,698 B2 | 2/2007 | Klosterman et al. |
| 7,191,007 B2 | 3/2007 | Desai |
| 7,209,792 B1 | 4/2007 | Parramon et al. |
| 7,226,442 B2 | 6/2007 | Sheppard, Jr. |
| 7,379,774 B2 | 5/2008 | Gord |
| 7,379,775 B2 | 5/2008 | Parramon et al. |
| 7,428,438 B2 | 9/2008 | Parramon et al. |
| 7,437,193 B2 | 10/2008 | Parramon et al. |
| 7,486,048 B2 | 2/2009 | Tsukamoto |
| 7,515,012 B2 | 4/2009 | Schulman |
| 7,555,345 B2 | 6/2009 | Wahlstrand et al. |
| 7,587,246 B2 | 9/2009 | Hochmair |
| 7,657,320 B2 | 2/2010 | Chadwick |
| 7,780,613 B2 | 8/2010 | Sherman |
| 7,912,551 B2 | 3/2011 | Wosmek et al. |
| 7,917,226 B2 | 3/2011 | Nghiem |
| 7,957,804 B2 | 6/2011 | Abreu |
| 2002/0177884 A1 | 11/2002 | Ahn et al. |
| 2002/0188333 A1 | 12/2002 | Nowick |
| 2004/0068298 A1 | 4/2004 | Parramon et al. |
| 2005/0055068 A1 * | 3/2005 | Von Arx et al. ............. 607/60 |
| 2005/0075693 A1 | 4/2005 | Toy et al. |
| 2005/0075697 A1 | 4/2005 | Olson |
| 2005/0119716 A1 | 6/2005 | McClure |
| 2005/0131495 A1 | 6/2005 | Parramon |
| 2005/0288739 A1 | 12/2005 | Hassler et al. |
| 2006/0020306 A1 | 1/2006 | Davis et al. |
| 2007/0060967 A1 * | 3/2007 | Strother et al. ............. 607/31 |
| 2008/0027513 A1 | 1/2008 | Carbunaru |
| 2008/0039903 A1 | 2/2008 | Chadwick |
| 2008/0051854 A1 | 2/2008 | Bulkes |
| 2008/0172109 A1 | 7/2008 | Rahman et al. |
| 2009/0018618 A1 | 1/2009 | Parramon et al. |
| 2009/0118796 A1 | 5/2009 | Chen et al. |
| 2009/0216296 A1 | 8/2009 | Meskens |
| 2009/0281597 A1 | 11/2009 | Parramon et al. |
| 2010/0069992 A1 | 3/2010 | Aghassian |
| 2010/0179618 A1 | 7/2010 | Marnfeldt |
| 2010/0204756 A1 | 8/2010 | Aghassian |
| 2010/0219796 A1 | 9/2010 | Kallmyer |
| 2010/0328077 A1 | 12/2010 | Stein |
| 2011/0112610 A1 | 5/2011 | Rahman et al. |
| 2011/0112611 A1 | 5/2011 | Aghassian |

OTHER PUBLICATIONS

"An Implantable Bionic Network of Injectable Neural Prosthetic Devices: The Future Platform for Functional Electrical Stimulation and Sensing to Restore Movement and Sensation", Library of Congress, BioMedical Engineer Fundamentals, p. 34-1-p. 34-18.

Tang et al., "Data Transmission from an Implantable Biotelemeter by Load-Shift Keying, Using Circuit Configuration Modulation", IEEE Transactions BioMedical Engineer, vol. 5, May 5, 1993, pp. 524-528.

Zierhofer, "A Class E Tuned Power Oscillator for Inductive Transmission of Digital Data & Power", IEEE Transactions BioMedical Engineer, 1991, pp. 782-792.

U.S. Appl. No. 13/019,568, filed Feb. 2, 2011.

U.S. Appl. No. 13/096,073, filed Apr. 28, 2011.

PCT/US2011/023463 International Search Report mailed May 6, 2011.

U.S. Appl. No. 13/019,568 Office Action Aug. 15, 2012.

U.S. Appl. No. 13/019,568 Response filed Sep. 10, 2012.

U.S. Appl. No. 13/019,568 Office Action Oct. 15, 2012.

Majerus et al., "Telemetry Platform for Deeply Implanted Biomedical Sensors", IEEE Xplore, pp. 1-6.

* cited by examiner

IMPLANTABLE MEDICAL DEVICES AND SYSTEMS HAVING POWER MANAGEMENT FOR RECHARGE SESSIONS

TECHNICAL FIELD

Embodiments relate to implantable medical devices and systems that utilize a recharge session to replenish battery life. More particularly, embodiments relate to implantable medical devices and systems that provide power management to address overcharge conditions.

BACKGROUND

Implantable medical devices (IMD) may provide a variety of different therapies and other functions including stimulation, drug infusion, physiological sensing, and the like. The IMDs receive programming from an external device and may also share information that has been collected with the external device. Many IMD communicates with the external device using an inductive form of telemetry where a telemetry head is held in communication range of the IMD so that inductive signals may be exchanged.

IMDs operate on battery power and therefore have a limited lifetime of operation before a replacement or a recharge is necessary. For IMDs that are capable of recharging the battery, the recharge energy is also received via an inductive coupling. The external device has a coil tuned to a recharge frequency, e.g., 5 kilohertz, that differs from the telemetry frequency. The IMD conventionally has a second coil that is tuned to the recharge frequency being emitted by the external device.

During the recharge process, an excessive amount of power may be coupled into the coil for various reasons. For example, the external device may be providing more power than is needed. As another example, the recharge coil of the IMD may be receiving energy from additional nearby sources of inductive energy. In such a case, there may be an overcharge condition that occurs where there is the potential to supply an excessive current or voltage to the battery.

SUMMARY

Embodiments address issues such as these and others by providing power management functions within the IMD of the medical system. The IMD may limit the potentially excessive current and/or voltage from reaching the battery such as by employing a recharge limiter and taking additional steps including turning the resonant frequency of the oscillatory circuit that includes the coil to a frequency other than a frequency of the recharge energy. Furthermore, various embodiments may provide for dissipation of this excessive current and/or voltage in various ways. For instance, embodiments may provide for communicating with the external device to request that the recharge power be decreased, by adding resistance to the oscillatory circuit, and/or by clamping the oscillatory circuit to ground.

Embodiments provide an implantable medical device that includes a tank circuit having a variable reactance. A battery is present with a rectifier between the battery and the tank circuit. A controller is in electrical communication with the variable reactance, and the controller includes logic to set the variable reactance to a first value when receiving recharge energy and to set the variable reactance to a second value upon detecting an overcharge condition while receiving recharge energy. Medical circuitry is in electrical communication with the battery.

Embodiments provide an implantable medical device that includes a tank circuit having a coil and capacitance. A battery is present with a rectifier between the battery and the tank circuit. A capacitor low side switch is coupled between the capacitance and ground and an inductor low side switch coupled between the coil and ground. A controller is in electrical communication with the capacitor low side switch and inductor low side switch, and the controller includes logic to close the capacitor low side switch and the inductor low side switch upon detecting an overcharge condition. Medical circuitry is in electrical communication with the battery.

Embodiments provide an implantable medical device that includes a tank circuit having a coil and capacitance. A battery is present with a rectifier between the battery and the tank circuit. A circuit pathway includes a switch in series with a resistor, and the circuit pathway is in parallel with the coil. A controller includes logic to set the switch of the circuit pathway to a first state while an overcharge condition is undetected, and to set the switch of the circuit pathway to a second state upon detecting the overcharge condition. Medical circuitry is in electrical communication with the battery.

Embodiments provide an implantable medical device that includes a tank circuit having a coil and capacitance. Drive circuitry is coupled to opposite sides of the tank circuit. A battery is present with a rectifier between the battery and the tank circuit. A controller is in electrical communication with the drive circuitry, and the controller includes logic to control the drive circuitry to ring the tank circuit when detecting an overcharge condition while receiving recharge energy. Medical circuitry is in electrical communication with the battery.

Embodiments provide a medical system that includes an external device having an inductive charging module that emits recharge energy and a controller that activates the inductive charging module. The medical system further includes an implantable medical device that includes a tank circuit having a variable reactance. A battery is present with a rectifier between the battery and the tank circuit. A controller is in electrical communication with the variable reactance, and the controller includes logic to set the variable reactance to a first value when receiving recharge energy and to set the variable reactance to a second value upon detecting an overcharge condition while receiving recharge energy. Medical circuitry is in electrical communication with the battery.

Embodiments provide a medical system that includes an external device having an inductive charging module that emits recharge energy and a controller that activates the inductive charging module. The medical system further includes an implantable medical device that includes a tank circuit having a coil and a capacitance. A battery is present with a rectifier between the battery and the tank circuit. A capacitor low side switch is coupled between the capacitance and ground, and an inductor low side switch is coupled between the coil and ground. A controller is in electrical communication with the capacitor low side switch and inductor low side switch, and the controller includes logic to close the capacitor low side switch and the inductor low side switch upon detecting an overcharge condition. Medical circuitry is in electrical communication with the battery.

Embodiments provide a medical system that includes an external device having an inductive charging module that emits recharge energy and a controller that activates the inductive charging module. The medical system further includes an implantable medical device that includes a tank circuit having a coil and a capacitance. A battery is present with a rectifier between the battery and the tank circuit. A circuit pathway includes a switch in series with a resistor, and the circuit pathway is in parallel with the coil. A controller includes logic to set the switch of the circuit pathway to a first state while an overcharge condition is undetected, and to set the switch of the circuit pathway to a second state upon detecting the overcharge condition. Medical circuitry is in electrical communication with the battery.

Embodiments provide a medical system that includes an external device having an inductive charging module that emits recharge energy and a controller that activates the inductive charging module. The medical system further includes an implantable medical device that includes a tank circuit having a coil and capacitance. Drive circuitry is coupled to opposite sides of the tank circuit. A battery is present with a rectifier between the battery and the tank circuit. A controller is in electrical communication with the drive circuitry, the controller includes logic to control the drive circuitry to ring the tank circuit when detecting an overcharge condition while receiving recharge energy. Medical circuitry is in electrical communication with the battery.

DETAILED DESCRIPTION

Embodiments provide for medical systems including IMDs that offer power management during a recharge session. The power management may utilize various manners of avoiding overcharging the battery by detecting overcharging and then taking a particular course of action. The circuit for the receiving coil may be tuned to a frequency other than a frequency of the recharge energy. Uplink telemetry may be used to request that the external device decrease the recharge power. Resistance may be added to reduce the Q of the circuit of the receiving coil. Furthermore, the circuit for the receiving coil may be clamped to ground.

Power management features may be included in conjunction with various other features. For instance, in some embodiments, the coil used for recharge may also be used for the uplink telemetry that is used for the request to reduce recharge power and may also be used for ordinary uplink telemetry sessions at a telemetry frequency other than the recharge frequency. Furthermore, in some embodiments, the coil used for recharge may also be used for downlink telemetry at a telemetry frequency other than the recharge frequency. It will be appreciated that power management may be applied for the recharge application regardless of whether telemetry applications are present and regardless of whether telemetry applications utilize the same coil being used for recharge or utilize one or more different coils.

Figure 1:
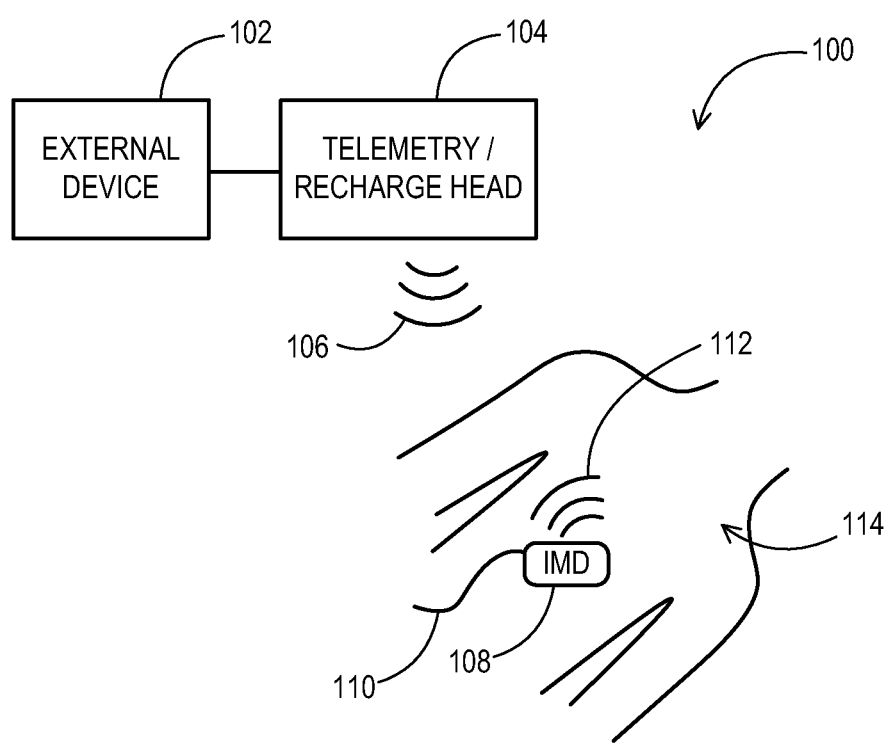
FIG. 1 shows a typical operating environment for a medical system including an external device and an IMD according to various embodiments.

FIG. 1 shows a typical operating environment for a medical system 100 that includes an external device 102 and an IMD 108. The external device 102 may provide programming and data collection services by using inductive telemetry. The external device 102 may also provide recharge services by using an inductive coupling. A telemetry/recharge head 104 that is tethered to the external device 102 may be placed nearby the patient's body 114 and in communication range of the IMD 108 so that an inductive coupling occurs between a coil within the head 104 and the coil within the IMD 108.

The head 104 may emit inductive signals 106 that represent downlink telemetry signals or recharge signals. The telemetry signals are emitted at one frequency while the recharge signals are emitted at a different time and at another frequency. For instance, the telemetry signals may be 175 kilohertz while the recharge signals are at 5 kilohertz. However, many different frequencies are possible for both telemetry and recharge and the recharge frequency may either be of a higher or lower frequency than the telemetry. While a single external device 102 is shown for both telemetry and recharge applications, it will be appreciated that these applications may be provided by different external devices where a first external device conducts a telemetry session at the telemetry frequency and a second external device conducts a recharge session at the recharge frequency at some other time.

Embodiments of the IMD 108 may utilize the same coil for the downlink and for the recharge. In such embodiments, the IMD 108 receives the inductive signals 106, including both the telemetry and the recharge signals, on the coil. Embodiments of the IMD 108 may additionally or alternatively utilize the same coil for the uplink and for the recharge. In such embodiments, the IMD 108 emits inductive telemetry signals 112 from the coil, and those signals are received by the coil of the head 104.

The IMD 108 of this example includes an extension 110 such as a medical lead or a catheter that allows the IMD 108 to perform one or more medical functions. For instance, where the extension 110 is a medical lead, then IMD 108 may provide stimulation signals to the body 114 via electrodes on the lead and/or may sense physiological signals of the body 114 via the electrodes. Where the extension 110 is a catheter, the IMD 108 may infuse drugs into the body 114. These medical functions may be performed by the IMD 108 in accordance with programming received via the inductive telemetry signals and may be performed by using battery power that is replenished by the inductive recharge signals.

Figure 2:
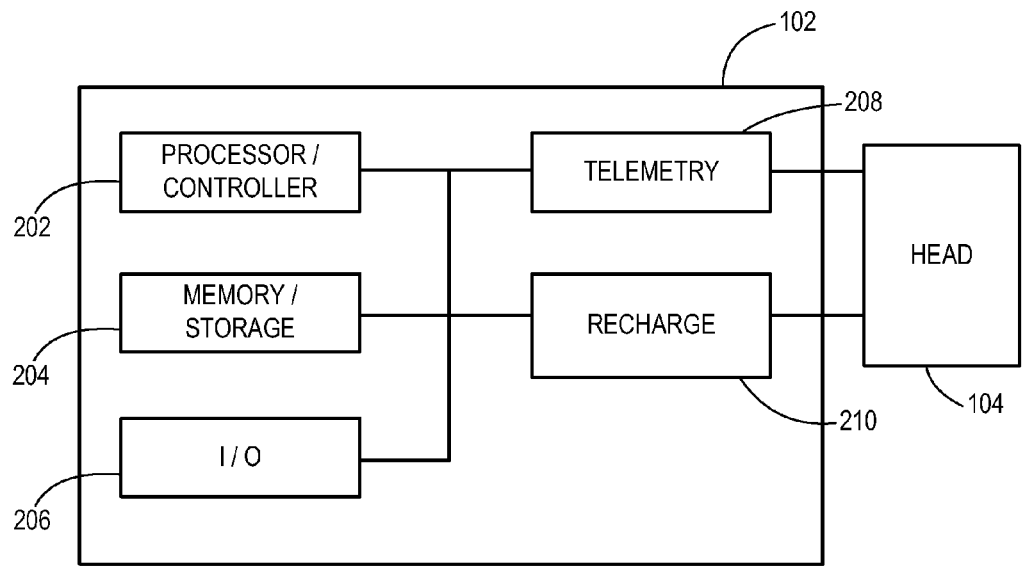
FIG. 2 shows a diagram of components of an example of an external device.

FIG. 2 shows components of one example of the external device 102. The external device 102 includes a processor/controller 202 and memory/storage device(s) 204. The external device 102 may also include local input/output (I/O) ports 206 such as to provide local screen displays and to receive user input via keyboard, mouse, and so forth. The external device 102 also includes a telemetry module 208 used to establish the telemetry to the IMD 108, and the telemetry module 208 may provide signals at the telemetry frequency to the head 104 during telemetry sessions. The external device of this example also includes a recharge module 210 used to transfer recharge energy to the IMD 108, and the recharge module 210 may provide signals at the recharge frequency to the head 104 during recharge sessions.

The memory/storage devices 204 may be used to store information in use by the processor 202. For instance, the memory/storage 204 may store therapy parameters that are input by a clinician or patient that are to be downlinked into the IMD 104. The memory/storage devices 204 may also store programming that is used by the processor 202 to control the telemetry and recharge actions of the external device 102. The memory/storage devices 204 may be of various types, such as volatile, non-volatile, or a combination of the two. The memory storage devices 204 may be used to store information for a long term and may be of various types such as electronic, magnetic, and optical drives. The memory/storage devices 204 are examples of computer readable media that may store information in the form of computer programming, data structures, and the like.

The processor/controller 202 includes logic to perform various operations to allow telemetry and/or recharge sessions with the IMD 108. The processor/controller 202 may be of various forms. For instance, the processor/controller 202 may include a general-purpose programmable processor that executes software that is stored on the memory/storage devices 204 or elsewhere. Other examples include a dedicated purpose hardware circuit or hard-wired digital logic. The processor/controller 202 may communicate with the various other components through one or more data buses.

Figure 3:
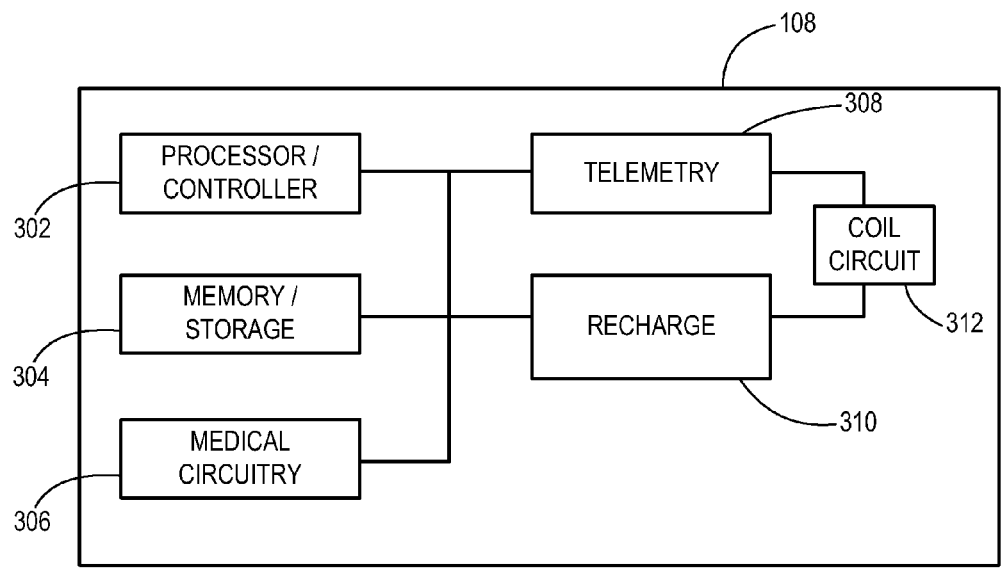
FIG. 3 shows a diagram of components of an example of an IMD.

FIG. 3 shows components of one example of the IMD 108. The IMD 108 includes a processor/controller 302 and a memory/storage device(s) 304. The IMD 108 also includes medical circuitry 306 that performs a medical task such as stimulation, drug delivery, monitoring, and the like. The IMD 108 of this example also includes telemetry circuitry 308 used to establish the uplink and/or downlink telemetry with the external device 102 in conjunction with single coil circuitry 312. The IMD 108 of this example further includes recharge circuitry 310 used to receive recharge energy from the external device 102 in conjunction with the single coil circuitry 312. As discussed above, it will be appreciated that the telemetry and recharge applications may instead utilize separate coils while the IMD 108 provides the power management features for the recharge application.

The memory/storage devices 304 may be used to store information in use by the processor/controller 302 such as programming and data values. The memory/storage devices 304 may store additional information including therapy parameters that are used to control the medical circuitry 306. The memory/storage devices 304 may be of various types such as volatile, non-volatile, or a combination of the two. The memory/storage devices 304 are also an example of computer readable media that may store information in the form of computer programming, data structures, and the like.

The processor/controller 302 includes logic to perform operations that allow telemetry and recharge sessions with the external device 102 to be established. The processor/controller 302 may be of various forms like those discussed above for the processor/controller 202 of the external device 102, such as a general purpose processor, an application specific circuit, hardwired digital logic, and the like. The processor/controller 302 may communicate with the various other components through one or more data buses. The processor/controller 302 may also control silicon based switches that are either integral to the processor/controller 302 or separate electronic devices to provide the telemetry, recharge, and power management functions while using the single coil or while using separate coils. These switches and other circuit details are discussed in more detail below with reference to FIGS. 4-24.

Figure 4:
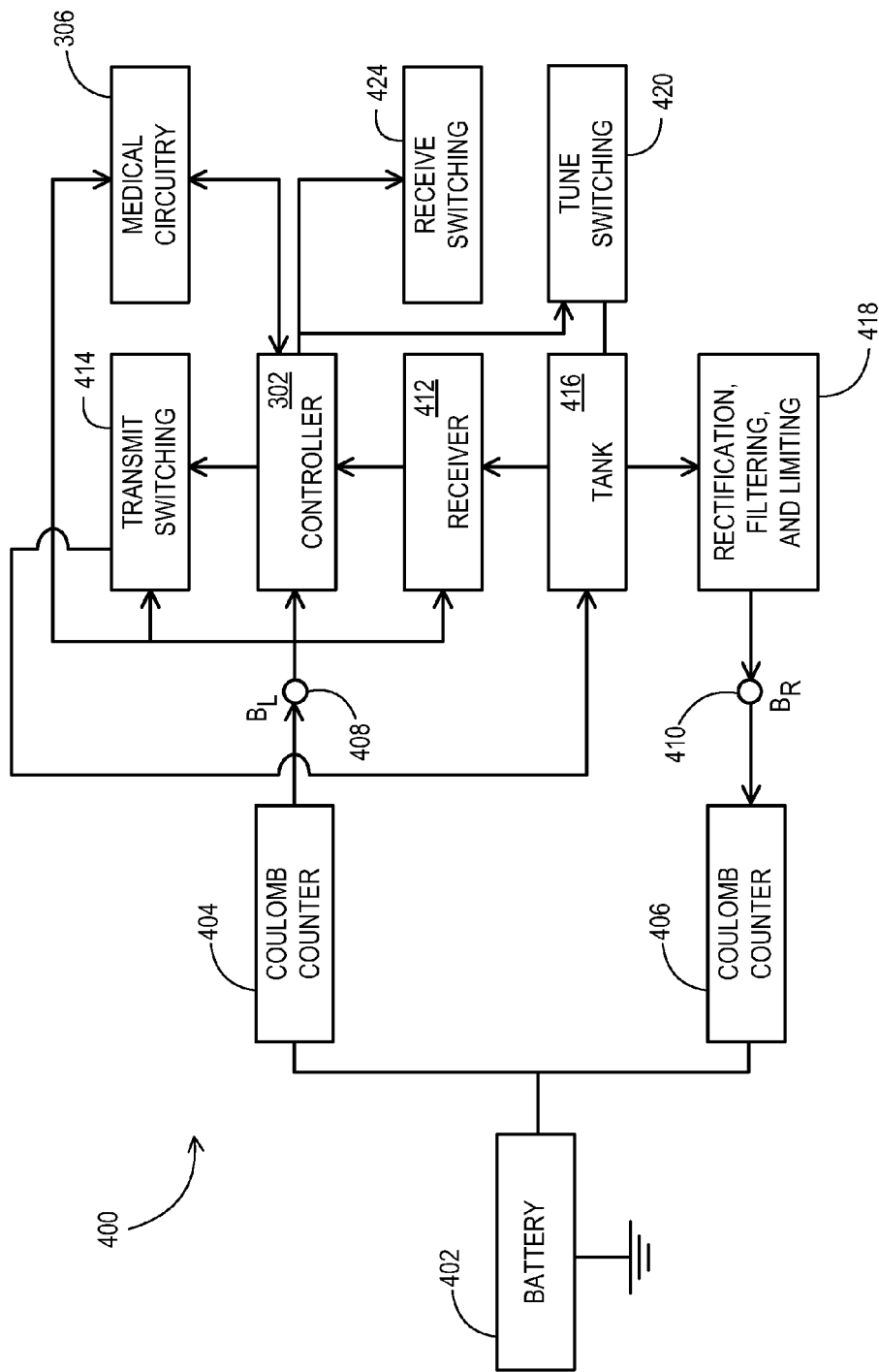
FIG. 4 shows a diagram of a load branch and a recharge branch of an example of an IMD.

FIG. 4 shows one example of a configuration 400 of circuit modules that may be employed in various embodiments of the IMD 108. This configuration 400 includes a battery 402 that provides the energy for the general operation of the IMD 108 including the operations being performed by the logic of the processor/controller 302 and the medical tasks being performed by the medical circuitry 306. The battery 402 also receives the energy being collected during the recharge session.

As shown, there is a load branch stemming from a node 408 and a recharge branch stemming from a node 410, where the node 408 and node 410 stem from the battery 402. In this example, each branch includes a Coulomb counter, 404, 406 where the Coulomb counter 404 for the load branch measures the amount of charge leaving the battery while the Coulomb counter 406 for the recharge branch measures the amount of charge entering the battery. The processor/controller 302 may gather this information to monitor the condition of the battery 402 as well as to report such information to the external device 102.

The node 408 sources power to several components. The processor/controller 302 receives power to operate including implementing the logic and output to control various switches that may vary the tuning frequency of the recharge coil and select between uplink, downlink, and recharge modes particularly for embodiments where a single coil is shared. In the case of a shared coil, drive circuitry such as an oscillator, for instance a sinusoidal power amplifier, or such as a set of transmitter switches 414 receive power to ultimately ring the coil to emit telemetry signals while a receiver 412 consumes power to receive and amplify the downlink telemetry signal and return it to the controller 302. The medical circuitry 306 receives power to perform the medical tasks such as pulse generation, drug infusion, data collection, and the like.

Several components receive control signals from the processor/controller 302. For embodiments where the coil is shared for telemetry and recharge applications, drive circuitry 414 may receive an activation signal in the case of an oscillator. The drive circuitry may receive timed control signals, discussed in more detail below with reference to FIGS. 20 and 21, in the case of transmitter switches that alternate their states in order to ring the coil at the telemetry frequency to uplink telemetry signals. A set of receiver switches 424 receive control signals to achieve a state that allows detection of the telemetry signal of the coil at the receiver 412. A tuning switch 420 receives a control signal to alter the state and ultimately vary the reactance of a tank circuit 416 that includes the coil so that one state tunes the tank circuit 416 for recharge while another state tunes the tank circuit 416 to a frequency other than the recharge frequency to provide power management by reducing the received power during recharge. For embodiments where the coil is shared with the telemetry application, this other frequency may be the telemetry frequency such that the tuning switch also establishes resonance for the coil at the telemetry frequency during telemetry sessions.

The node 410 of the recharge branch receives power from a power module 418. This power module 418 receives the recharge signal induced onto the coil of the tank circuit 416 by the incoming recharge signals. The power module 418 includes a rectifier, a filter, and a limiter so that the node 410 receives power that has a suitable voltage and current for recharging the battery 402.

The various switching modules of FIG. 4 have a default state such as where no control signal is present either by operation of the processor/controller 302 or as a result of a fully depleted battery 402. For embodiments where the coil is shared with the telemetry application, one configuration of the switches is such that when all switches are in the default state, the tank circuit 416 is tuned to the telemetry frequency with the tank circuit's output being directed into the rectifier of the power module 418. Thus, an attempt at communicating with the IMD 108 that is currently non-operational via telemetry may succeed in supplying enough recharge energy to the battery 402 to allow the processor/controller 302 to become operational and respond. Examples of specific circuits such as those that are shown in FIGS. 5-19 and 22-24 and others that are discussed below implement the modules of FIG. 4 while providing the default state that allows for recharge at the telemetry frequency.

Figure 5:
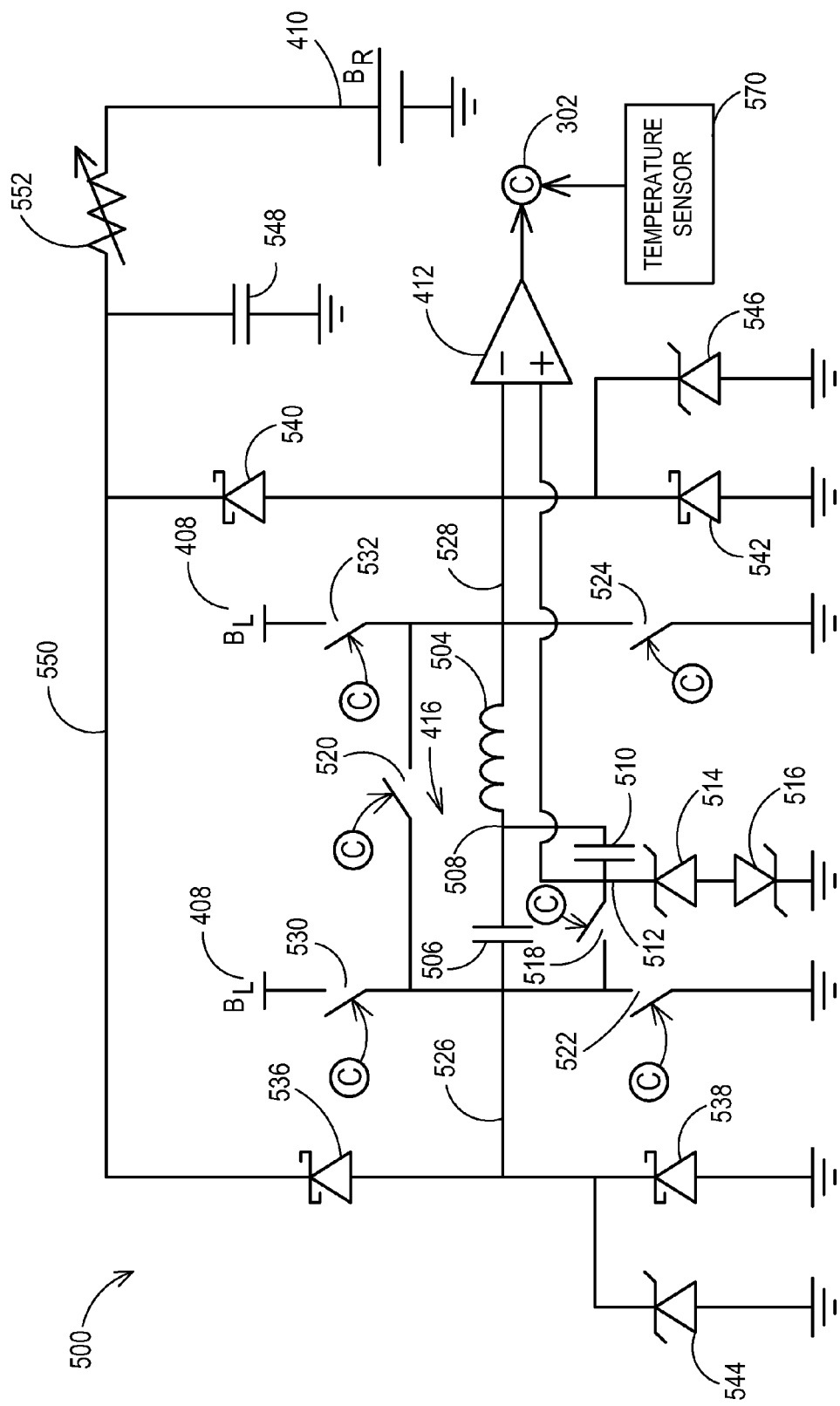
FIG. 5 shows a circuit of one example of an IMD that utilizes power management while providing for telemetry uplink and telemetry downlink at one frequency and recharge at another frequency with a single coil and variable capacitance with a first receiver configuration and a first rectifier configuration.

FIG. 5 shows a first configuration 500 for a circuit that provides for telemetry uplink and downlink at a telemetry frequency as well as providing for recharge with power management at a different frequency while using a single coil. As discussed above, the first configuration 500 includes switches implemented in silicon with a default state that is open which allows for recharge mode to occur at the telemetry frequency when the IMD 108 is non-operational due to a depleted battery.

The first configuration includes the tank circuit 416 that has a coil 504 and the variable reactance is provided by a variable capacitance. The variable capacitance is achieved in this example by providing a first capacitor 506 that is hardwired in series with the coil 504 and by providing a second capacitor 510 that is switched into and out of a parallel relationship with the first capacitor 506 by a tuning switch 518, which is implemented in silicon and is under the control of the processor/controller 302. The processor/controller 302 may open and close the tuning switch 518 to vary the capacitance of the tank circuit and thereby tune the resonant frequency of the tank circuit 416 to either the telemetry or the recharge frequency.

In this particular example, the telemetry frequency is higher than the recharge frequency and so the coil 504 is tuned to the telemetry frequency when less capacitance is present. It will be appreciated that the opposite design could be employed where the recharge frequency is higher and thus some capacitance is switched out of the circuit to tune the coil 504 to the recharge frequency.

The tank circuit 416 establishes several nodes. An inductor side node 528, a capacitor side node 526, and a high voltage node 508 are achieved. The high voltage node 508 acquires a relatively high voltage periodically as the voltage swings within the tank circuit 416. An additional capacitor side node 512 is present particularly when the tuning switch 518 is open.

The capacitor side node 526 and inductor side node 528 are connected to a rectifier that is established by a set of diodes 536, 538, 540, and 542 that may be of the Schottky variety. These diodes form a full-bridge rectifier. However, a capacitor low side switch 522 and an inductor low side switch 524 are present and either one may be closed by the processor/controller 302 to provide a half-wave rectifier.

As an alternative rectifier for this configuration, the capacitor low side switch 522 and the inductor low side switch 524 may be operated as low-side synchronous rectifier switches. In such a case, the state machine control of these switches 522, 524 by the processor/controller 302 operates by closing the capacitor low side switch 522 while leaving the inductor low side switch 524 open when the inductor side node 528 flies high and by closing the inductor low side switch 524 while leaving the capacitor low side switch 522 open when the capacitor side node 526 flies high. Other rectifier options are discussed with reference to other circuit diagrams below.

A capacitor side Zener diode 544 and an inductor side Zener diode 546 are also present. These devices limit voltage swings on the capacitor side node 526 and the inductor side node 528 to prevent over-voltage damage from occurring on voltage sensitive devices connected to these nodes. Voltage sensitive devices may include the various switches which are implemented in silicon and particularly those that are implemented as monolithic devices. Likewise, Zener diodes 514 and 516, shown in an anode-to-anode relationship but could be in a cathode-to-cathode relationship, are present to prevent over-voltage damage from occurring on additional voltage sensitive devices such as the tuning switch 518 on the additional capacitor side node 512. These devices may be actual Zener diodes or may be other devices which have Zener-like behavior.

The high voltage node 508 achieves the highest voltage during voltage swings within the tank circuit 416. As can be seen, no voltage sensitive device is DC coupled to the high voltage node which reduces the likelihood of any damage to those voltage sensitive devices. While the additional capacitor side node 512 may also achieve the relatively high voltage during telemetry by being AC coupled to the high voltage node 508 via the second capacitor 510, the Zener diodes 514, 516 provide additional protection for the tuning switch 518.

The rectifier provides voltage to a rectifier recharge node 550. This rectifier recharge node 550 also includes a filtering capacitor 548 in parallel with the rectifier. A current or voltage limiter 552 is in series between the rectifier recharge node 550 and the battery recharge node 410 to prevent the battery 402 from receiving voltage and/or current in excess of the amounts rated for the battery 402.

This embodiment of the IMD 108 is also capable of telemetry downlink by using the tank circuit 416. The receiver 412 may be present to receive the telemetry signals induced on the coil 504. The receiver 412 is connected to the tank circuit in a first configuration in the example of FIG. 5. Other configurations are discussed below with reference to other figures. In this example, a first input of the receiver 412 is connected to the inductor side node 528 while a second input of the receiver 412 is connected to the additional capacitor side node 512. In this manner the second input of the receiver 412 is capacitively coupled to the high voltage node 508 via the second capacitor 510 regardless of the state of the tuning switch 518. As the input impedance of the receiver 412 is very high, the receiver 412 does not appreciably affect the tuning of the tank circuit 416.

Rather than the receiver 412 being used as a telemetry downlink receiver, the receiver 412 may additionally or alternatively be used as a signal amplifier tool for measuring current and/or voltage in the tank circuit 416 during recharge so that the processor/controller 302 may detect an overcharge condition. This signal amplifier feature that is used during recharge is applicable to all of the embodiments discussed below in FIGS. 6-18 that also include the receiver 412. A temperature sensor 570 may also be included, as shown in FIG. 5, for all of the embodiments of FIGS. 5-18 in conjunction with the signal amplifier tool to provide the processor/controller 302 with an additional indicator of an overcharge condition by measuring the heat being dissipated within the IMD 108.

A tank switch 520 is included between the capacitor side node 526 and the inductor side node 528. This tank switch 520 when closed can effectively bypass the rectifier during the downlink telemetry. Other options for downlink telemetry where the tank switch 520 is left open or omitted are discussed below in relation to other figures.

This embodiment of the IMD 108 is also capable of telemetry uplink by using the tank circuit 416 and one of various methods. For instance, as shown, an H-bridge may be provided in relation to the tank circuit 416 by connecting a capacitor high side switch 530 between the load node 408 and the capacitor side node 526 while also connecting an inductor high side switch 532 between the load node 408 and the inductor side node 528.

The various modes of operation of the configuration 500 operate as follows. During recharge mode when using full wave rectification, the processor/controller 302 of this example sets the tuning switch 518 to the state that provides the proper capacitance for setting the resonant frequency of the tank circuit 416 to the recharge frequency. All other switches remain open. As a result, the current of the tank circuit passes through the rectifier and on to the limiter and ultimately to the battery 402. If half wave rectification is desired, then either capacitor low side switch 522 or inductor low side switch 524 is closed.

During recharge, the overcharge condition is addressed by the limiter 552 increasing impedance which pumps up voltage on the rectifier recharge node 550 to a Schottky drop below the peak voltage on the capacitor side node 526 and inductor side node 528. The peak voltage on these two nodes is set by the Zener diodes 544, 546. If a large amount of energy continues to be coupled into the coil 504, then the Zener diodes 544, 546 may be subjected to significant heating which can be problematic.

In such a case, the processor/controller 302 may detect such heating or overcharge via the aforementioned temperature sensor and/or other measurement device such as the signal amplifier tool represented by the receiver 412 and respond in various ways. For instance, the processor/controller 302 may change the state of the tuning switch 518 so that the coupling coefficient between the coil 504 and the coil of the external device 102 is decreased, thereby decreasing the power being received. Additionally or alternatively, the processor/controller 302 may close the capacitor low side switch 522 and the inductor low side switch 524 to clamp the tank circuit 416 to ground, as the coil 504, capacitors 506, 510, and Zener diodes 514, 516 together may be better suited to dissipate the heat as part of the larger system. The processor/controller 302 may also utilize telemetry uplink, which is discussed in more detail below, to request that the external device 102 decrease the recharge power.

During telemetry downlink, the processor/controller 302 of this example sets the tuning switch 518 to the opposite state from that set for recharge so that the proper capacitance for setting the resonant frequency of the tank circuit 416 to the telemetry frequency is achieved. The tank switch 520 is then closed. All other switches are left open, and the capacitor side node 526 and the inductor side node 528 are allowed to float within a diode drop below ground and above rectifier recharge node 550, respectively. The receiver 412 picks up the differential voltage across the coil 504. Several other methods of telemetry downlink are discussed below with reference to other circuit diagrams.

During telemetry uplink, such as when the processor/controller 302 determines that a request should be sent to the external device 102 to decrease recharge power, the H-bridge may be operated by opening the capacitor high side switch 530 and the inductor low side switch 524 while the inductor high side switch 532 and the capacitor low side switch 522 are closed. After a set amount of time defined by the telemetry frequency, the inductor high side switch 532 and the capacitor low side switch 522 are opened while the capacitor high side switch 530 and the inductor low side switch 524 are closed. These pairings continue to alternate states to ring up the coil 504 and allow it to emit for a set amount of time. The capacitor low side switch 522 and the inductor low side switch 524 are then closed to ring down the coil 504, which remains off for a set period until time to again ring up the coil 504. In this manner, a carrier on/off protocol can be effectively implemented to uplink data. As an alternative, the coil 504 may be allowed to ring down by closing the tank switch 520, closing switches 522 and 524 or by opening all switches and allowing the tank to ring down at its natural frequency.

Figure 20:
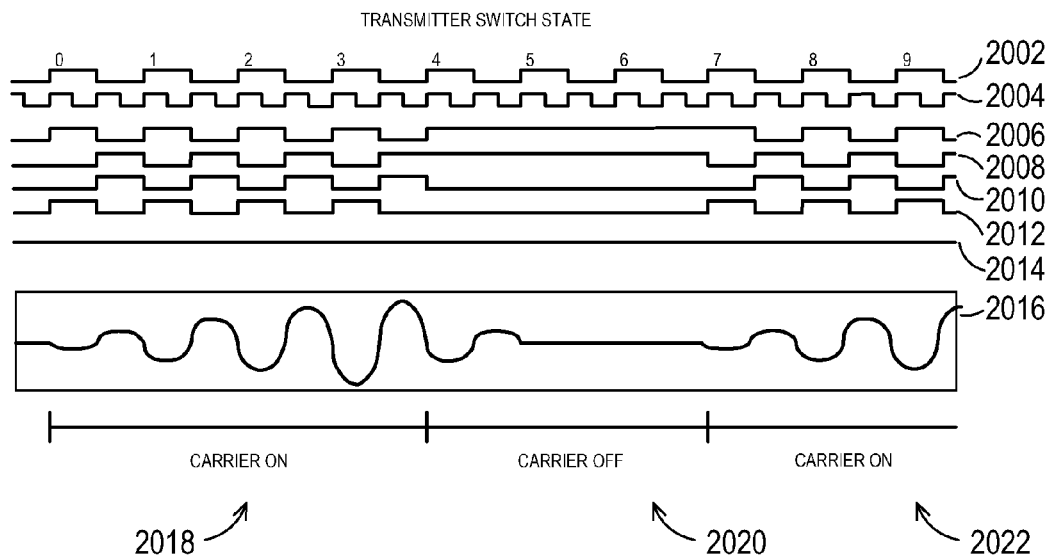
FIG. 20 shows a state of switches of one example of an IMD to establish telemetry uplink for various purposes including power management.

FIG. 20 shows a first timing chart for the H-bridge manner of telemetry uplink. The first waveform 2002 is a clock signal that is set to the telemetry frequency. The second waveform 2004 is a clock signal that is set to double the telemetry frequency but is unused in this particular method. The third and fourth waveforms 2006, 2008 correspond to the state of the capacitor low side switch 522 and the inductor low side switch 524, where a high value represents a closed state and a low value represents an open state. The fifth and sixth waveforms 2010, 2012 correspond to the state of the capacitor high side switch 530 and the inductor high side switch 532. The seventh waveform 2014 corresponds to the state of the tank switch 520 which remains open in this example.

The eighth waveform 2016 corresponds to the current through the coil 504. Sections 2018 and 2022 correspond to the ringing up and carrier on periods, while section 2020 corresponds to the carrier off period.

Figure 21:
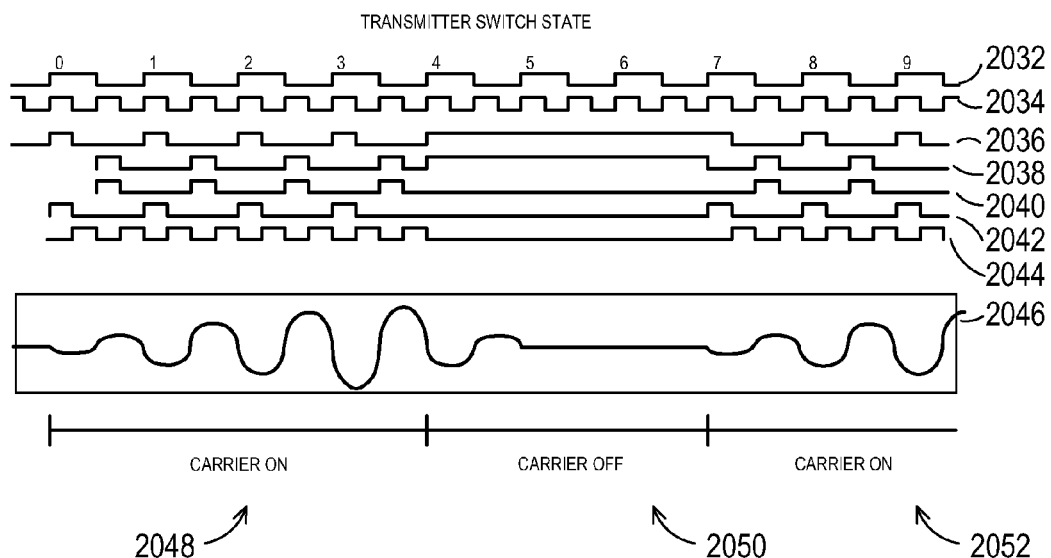
FIG. 21 shows an alternative state of switches of one example of an IMD to establish telemetry uplink for various purposes including power management.

FIG. 21 shows an alternative timing chart for the H-bridge manner of telemetry uplink where the transmission power is being throttled down by reducing the drive time of the coil 504. In this particular example, the drive time is being reduced by 50% by application of a clock frequency double that of the telemetry frequency, but other drive time reductions are applicable. Throttling down the transmission power may be done for various reasons, such as to reduce the range of the transmission for security or other purposes and/or to conserve energy. The drive time may be reduced more or less than the 50% shown in FIG. 21 for similar reasons.

The first waveform 2032 is a clock signal that is set to the telemetry frequency. The second waveform 2034 is a clock signal that is set to double the telemetry frequency. The third and fourth waveforms 2036, 2038 correspond to the state of the capacitor low side switch 522 and the inductor low side switch 524, where a high value represents a closed state and a low value represents an open state. The fifth and sixth waveforms 2040, 2042 correspond to the state of the capacitor high side switch 530 and the inductor high side switch 532. The seventh waveform 2044 corresponds to the state of the tank switch 520.

The eighth waveform 2046 corresponds to the current through the coil 504. Sections 2048 and 2052 correspond to the ringing up and carrier on periods, while section 2050 corresponds to the carrier off period.

As can be seen, the H-bridge switches are closed for half as long as in the example of FIG. 20, and the tank switch 520 is closed for the remaining half of each telemetry clock cycle portion when all the H-bridge switches are open. As a result, the current in the coil 504 rings up to a fraction of the amount of current achieved in the example of FIG. 20.

The telemetry uplink may be established in other ways as well by using switches on either side of the tank circuit 416 to ring the coil 504. For example, the capacitor low side switch 522 and the inductor high side switch 532 may be briefly closed, then opened while leaving the other switches open and then letting the tank circuit 416 ring down by closing the tank switch 520 or by closing both the capacitor low side switch 522 and the inductor low side switch 524.

Figure 6:
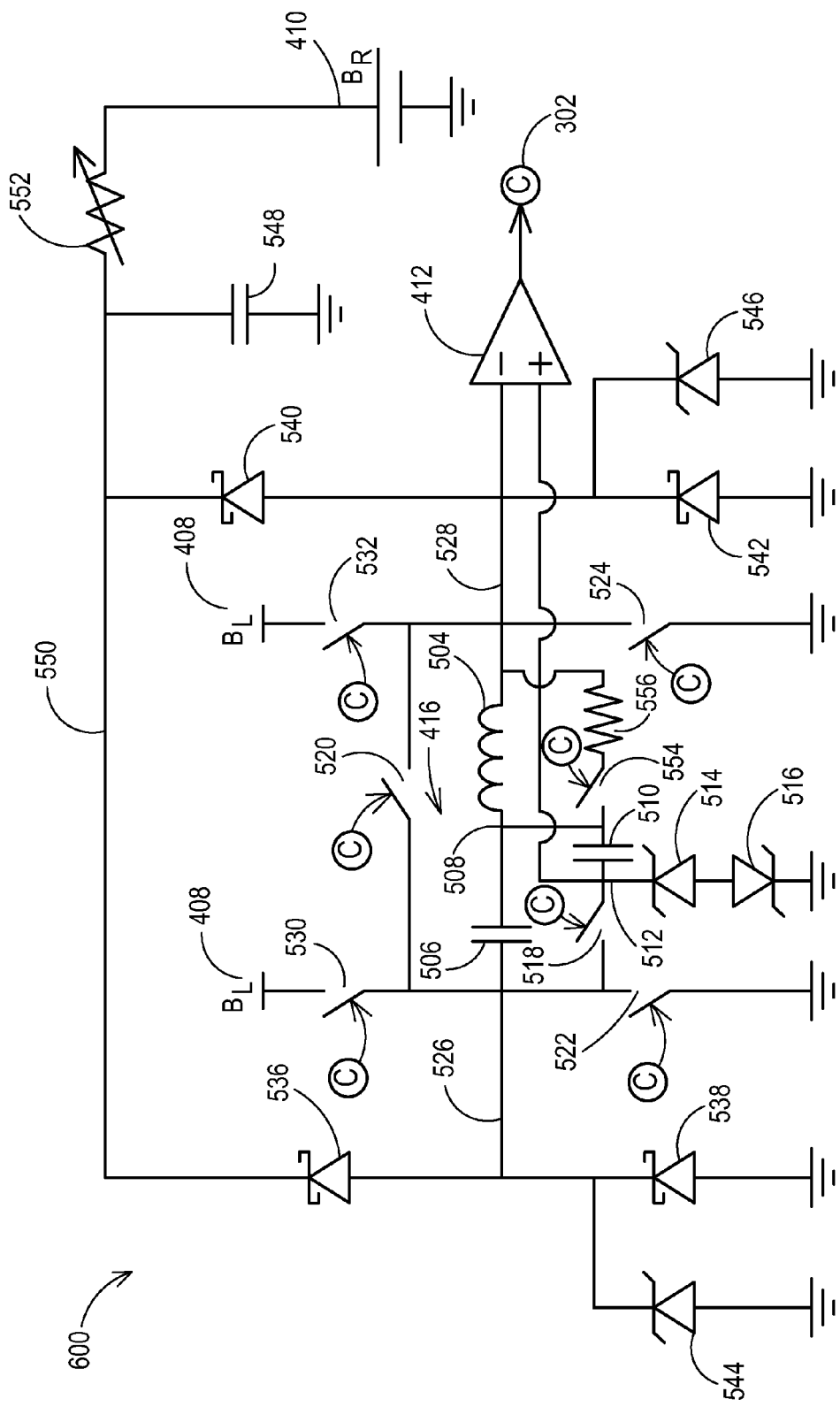
FIG. 6 shows a circuit of one example of an IMD that utilizes power management while providing for telemetry uplink and telemetry downlink at one frequency and recharge at another frequency with a single coil while including a snubbing resistor for power management and/or telemetry uplink.

FIG. 6 shows a second configuration 600 which is identical to the first configuration 500 of FIG. 5 except that a circuit pathway is provided that includes a snubbing resistor 556 and a snubbing switch 554 that is under control of the processor/controller 302 in parallel with the coil 504. This circuit pathway provides power management in the event of an overcharge condition in addition to or as an alternative to the power management methods discussed above for FIG. 5. Because the snubbing switch 554 may be closed to allow some tank circuit current to pass through the snubbing resistor to dissipate the energy as heat in that component and to lower the Q of the tank circuit 416, there is less energy to be dissipated by the Zener devices 542, 544 and 514, 516.

This circuit pathway including the snubbing switch 554 and snubbing resistor 556 may have other uses as well. For instance, the telemetry of the external device 102 may be configured to receive information by monitoring for a change in the mutual inductance between the coil of the external device 102 and the coil 504 of the IMD 108 that is caused by the IMD 108 while the external device 102 is emitting a signal. This change in the mutual inductance by the IMD 108 can be viewed as a transmission of information, for example where an on-off fashion of the change in mutual inductance is similar to a carrier on-off protocol. In such a case, the H-bridge may be unnecessary and the capacitor high side switch 530 and inductor high side switch 532 may be omitted, although low side switches 522 and 524 may be retained for other purposes such as to ground the tank circuit 416.

The circuit pathway including the snubbing switch 554 and the snubbing resistor 556 is shown in the configuration 600 of FIG. 6 as a modification to the configuration 500 of FIG. 5. However, it will be appreciated that this circuit pathway may be included as a modification to other configurations as well, including those discussed below in relation to FIGS. 7-19 and 22-24.

Figure 7:
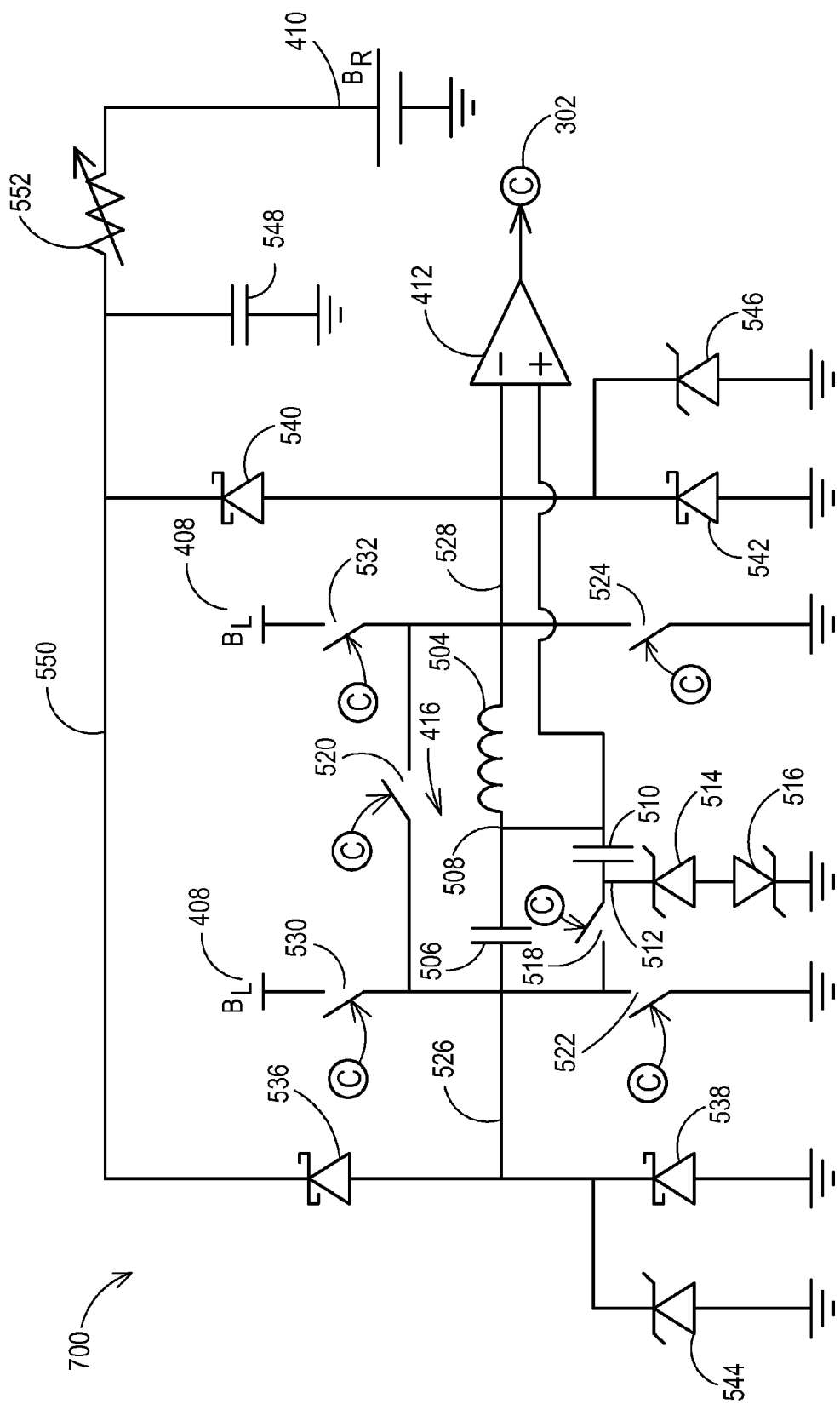
FIG. 7 shows a circuit of one example of an IMD that utilizes power management while providing for telemetry uplink and telemetry downlink at one frequency and recharge at another frequency with a single coil and with a second receiver configuration.

FIG. 7 shows another configuration 700 that is the same as the configuration 500 of FIG. 5 except that the receiver's connectivity is configured differently. In this example, a receiver input is coupled directly to the high voltage node 508, rather than being capacitively coupled through the second capacitor 510.

Figure 8:
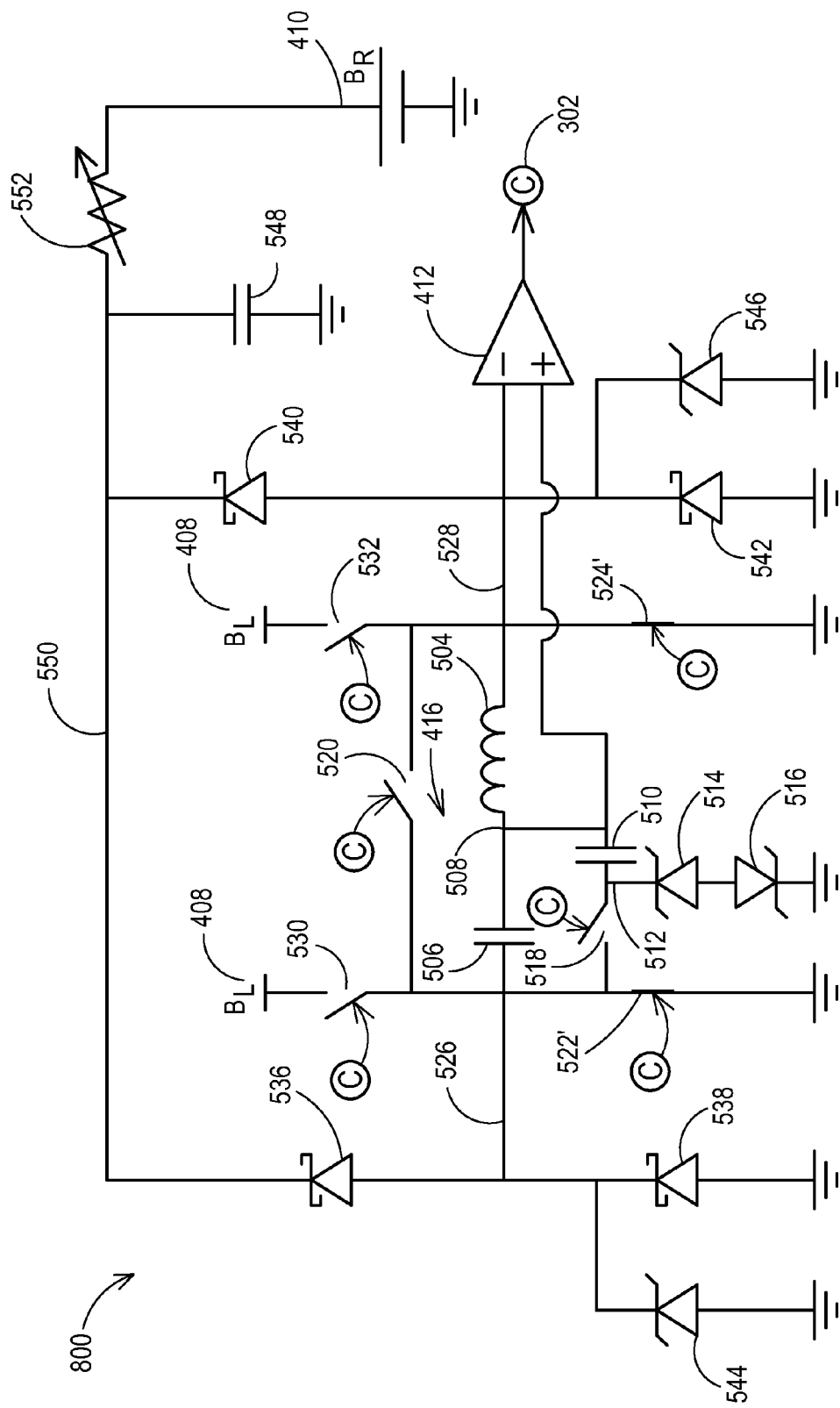
FIG. 8 shows a circuit of one example of an IMD that utilizes power management while providing for telemetry uplink and telemetry downlink at one frequency and recharge at another frequency with a single coil and with a third receiver configuration.

FIG. 8 shows another configuration 800 that is the same as the configuration 700 of FIG. 7 except that the receiver's connectivity is configured differently. In this example, a receiver input is coupled directly to the high voltage node 508, rather than being capacitively coupled through the second capacitor 510, but both the capacitor side node 526 and the inductor side node 528 are connected to ground by closed switches 522' and 524' when receiving telemetry signals while all other switches are open.

Figure 9:
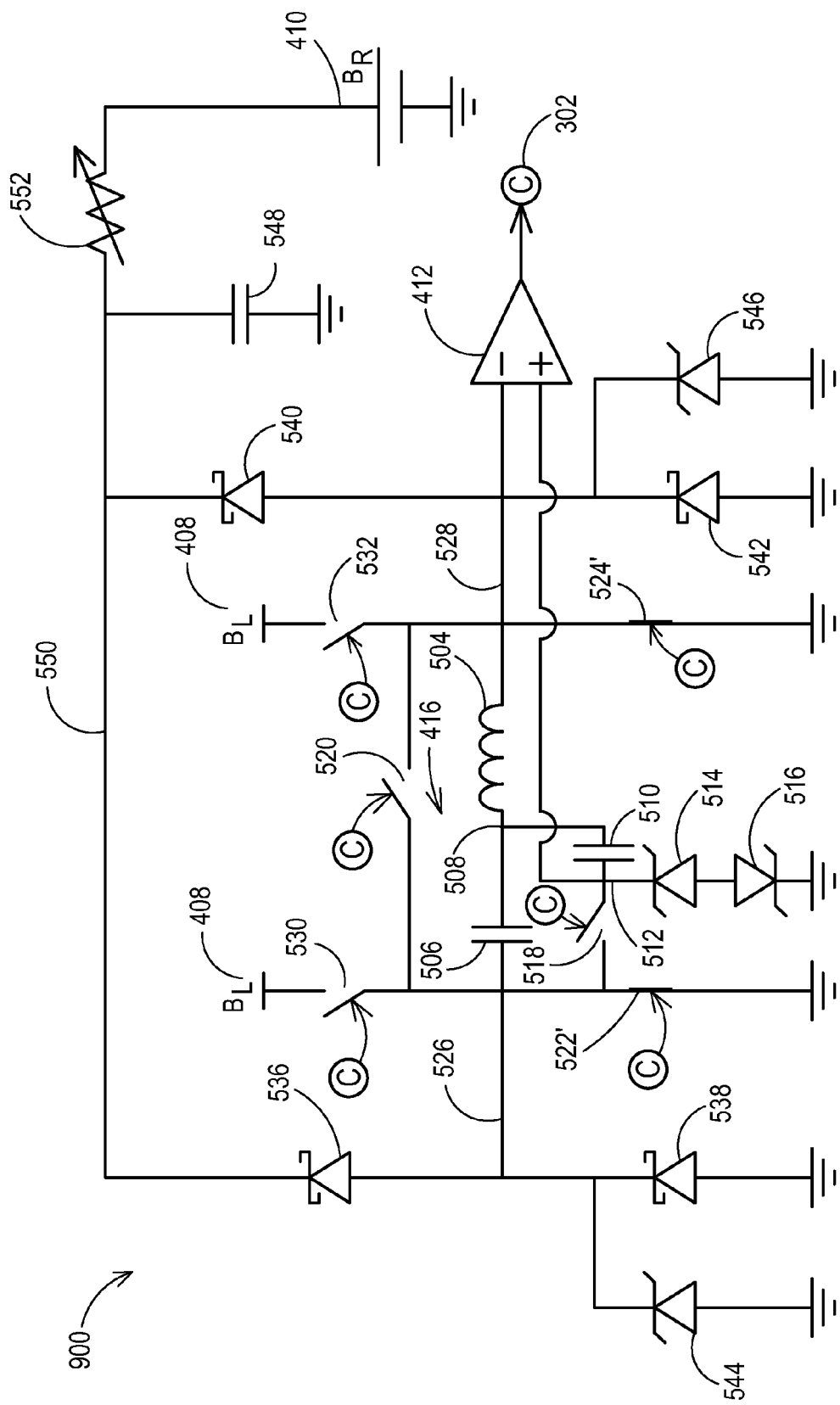
FIG. 9 shows a circuit of one example of an IMD that utilizes power management while providing for telemetry uplink and telemetry downlink at one frequency and recharge at another frequency with a single coil and with a fourth receiver configuration.

FIG. 9 shows another configuration 900 that is the same as the configuration 500 of FIG. 5 except that the receiver's connectivity is configured differently. In this example, a receiver input is capacitively coupled to the high voltage node 508 through the second capacitor 510, but both the capacitor side node 526 and the inductor side node 528 are connected to ground by closed switches 522' and 524' when receiving telemetry signals while all other switches are open.

Figure 10:
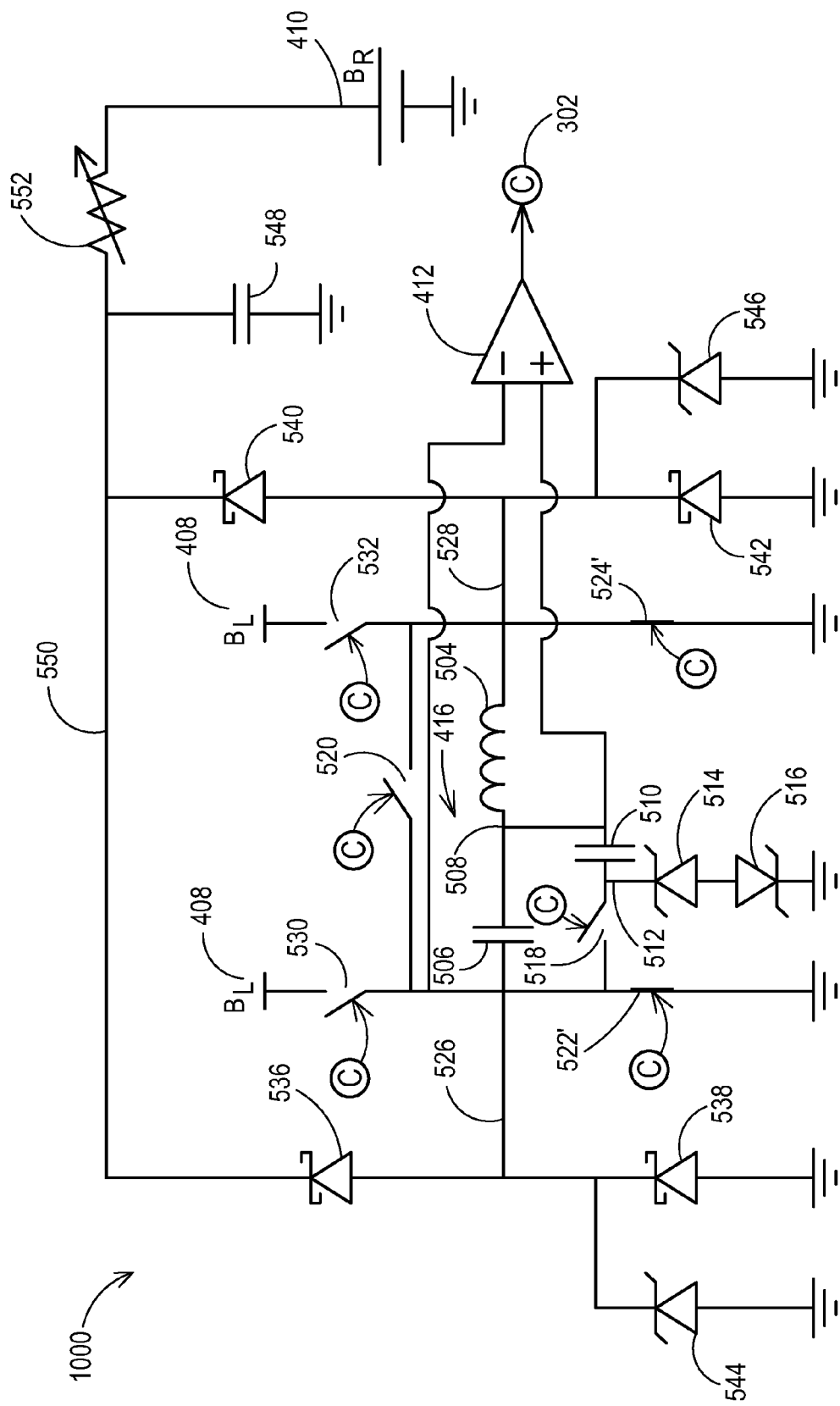
FIG. 10 shows a circuit of one example of an IMD that utilizes power management while providing for telemetry uplink and telemetry downlink at one frequency and recharge at another frequency with a single coil and with a fifth receiver configuration.

FIG. 10 shows another configuration 1000 that is the same as the configuration 800 of FIG. 8 except that the receiver's connectivity is configured differently. In this example, a receiver input is coupled directly to the high voltage node 508, rather than being capacitively coupled through the second capacitor 510, and both the capacitor side node 526 and the inductor side node 528 are connected to ground by closed switches 522' and 524' when receiving telemetry signals while all other switches are open. However, the other input of the receiver 412 is connected to the capacitor side node 526 rather than the inductor side node 528.

Figure 11:
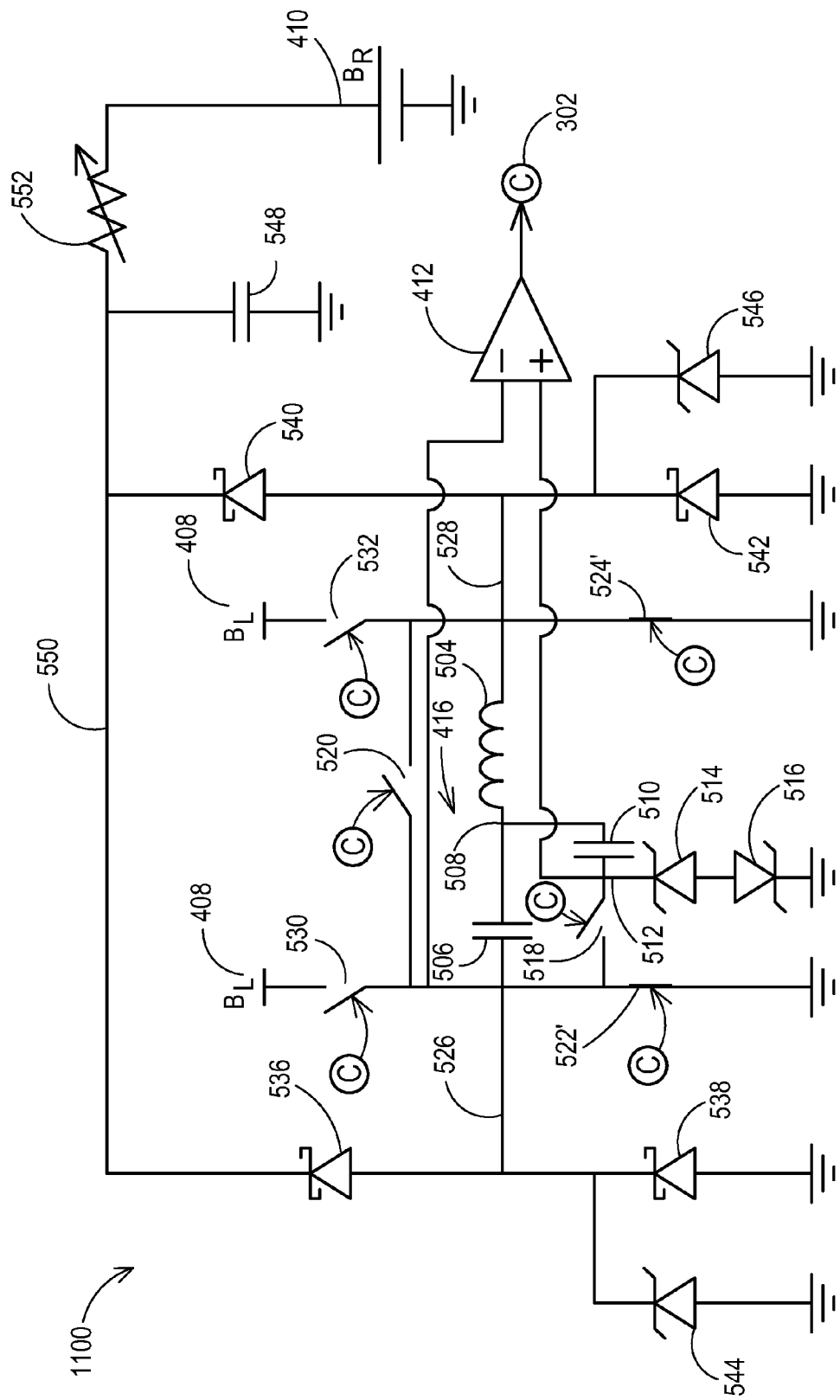
FIG. 11 shows a circuit of one example of an IMD that utilizes power management while providing for telemetry uplink and telemetry downlink at one frequency and recharge at another frequency with a single coil and with a sixth receiver configuration.

FIG. 11 shows another configuration 1100 that is the same as the configuration 900 of FIG. 9 except that the receiver's connectivity is configured differently. In this example, a receiver input is capacitively coupled to the high voltage node 508 through the second capacitor 510, and both the capacitor side node 526 and the inductor side node 528 are connected to ground by closed switches 522' and 524' when receiving telemetry signals while all other switches are open. However, the other input of the receiver 412 is connected to the capacitor side node 526 rather than the inductor side node 528.

Figure 12:
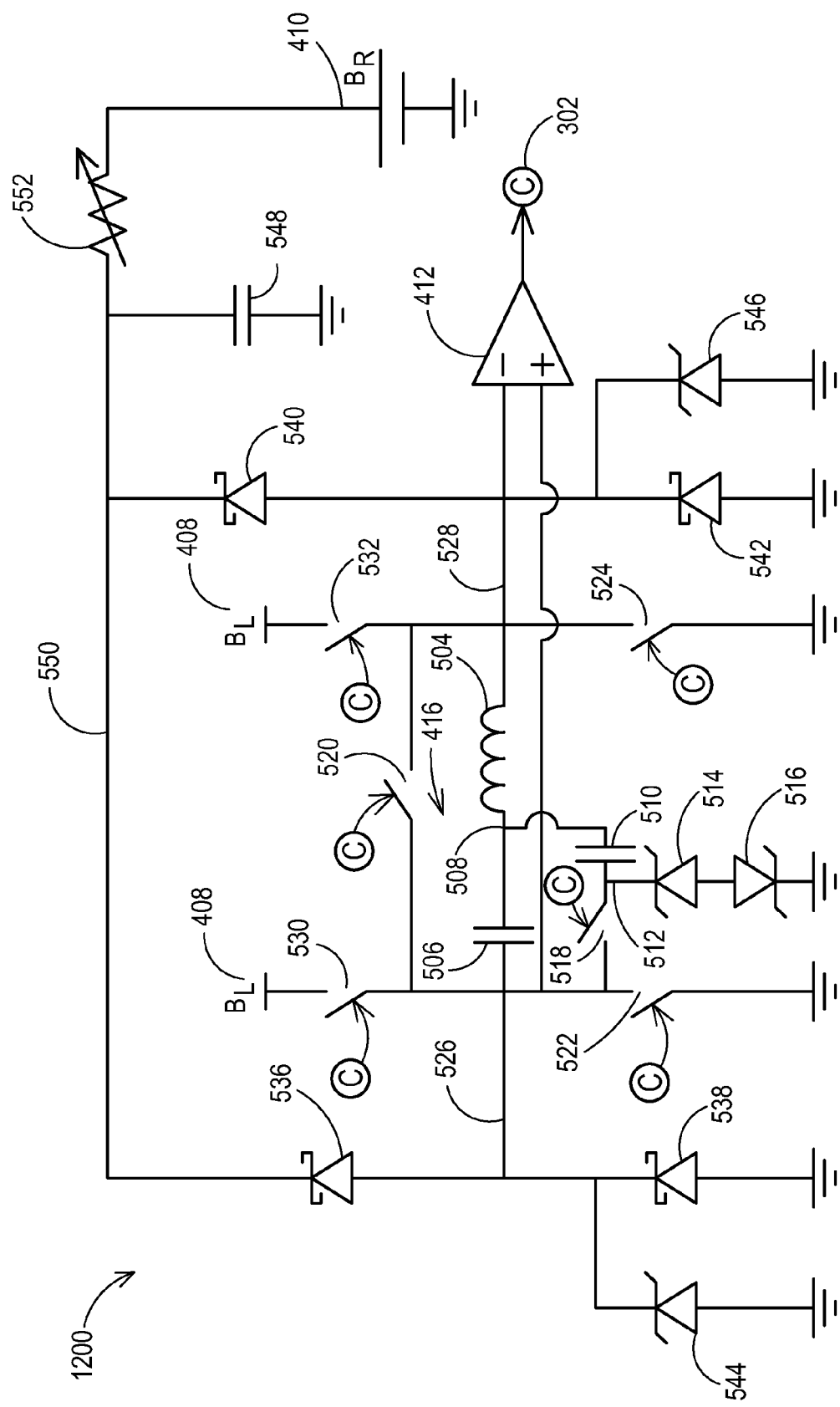
FIG. 12 shows a circuit of one example of an IMD that utilizes power management while providing for telemetry uplink and telemetry downlink at one frequency and recharge at another frequency with a single coil and with a seventh receiver configuration.

FIG. 12 shows another configuration 1200 that is the same as the configuration 500 of FIG. 5 except that the receiver's connectivity is configured differently. Here, the receiver is connected differentially across the tank circuit 416 by having a receiver input coupled directly to the inductor side node 528 while another receiver input is coupled directly to the capacitor side node 526. All other switches are open when receiving telemetry signals.

Figure 13:
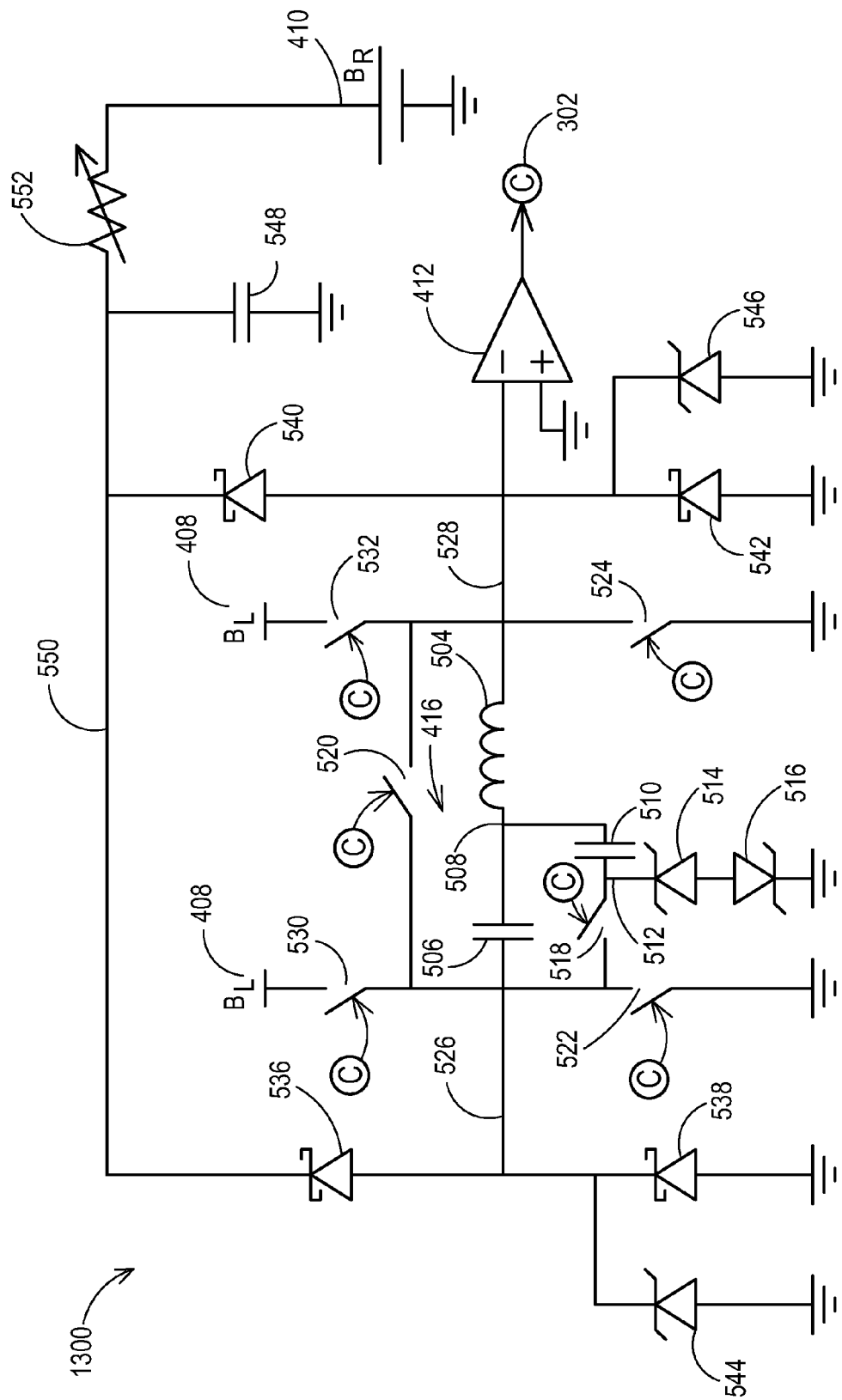
FIG. 13 shows a circuit of one example of an IMD that utilizes power management while providing for telemetry uplink and telemetry downlink at one frequency and recharge at another frequency with a single coil and with an eighth receiver configuration.

FIG. 13 shows another configuration 1300 that is the same as the configuration 500 of FIG. 5 except that the receiver's connectivity is configured differently. Here, one input of the receiver 412 remains connected to the inductor side node 528 while the other input of the receiver 412 is connected to ground. All other switches are open when receiving telemetry signals or switch 520 may be closed.

Figure 14:
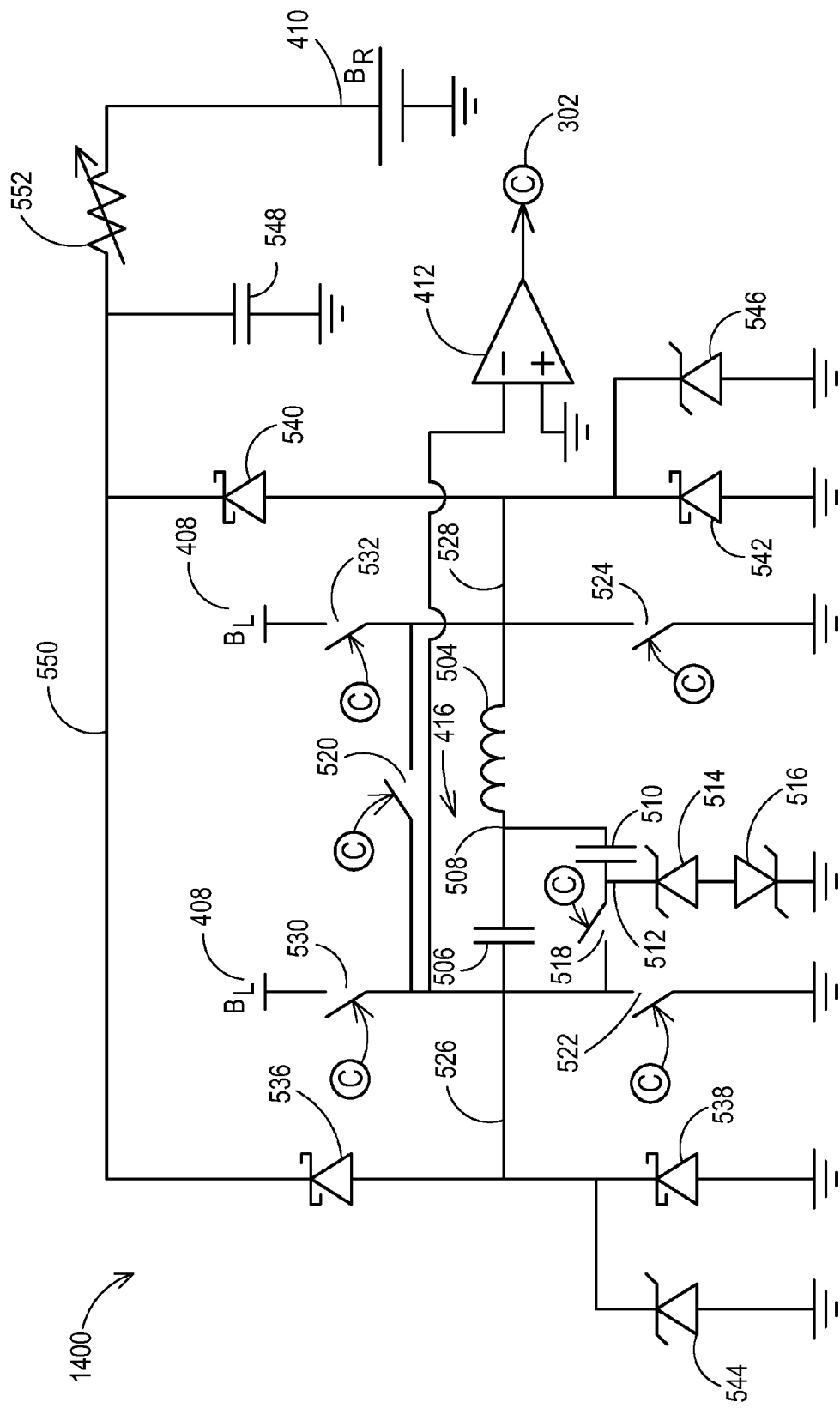
FIG. 14 shows a circuit of one example of an IMD that utilizes power management while providing for telemetry uplink and telemetry downlink at one frequency and recharge at another frequency with a single coil and with a ninth receiver configuration.

FIG. 14 shows another configuration 1400 that is the same as the configuration 500 of FIG. 5 except that the receiver's connectivity is configured differently. Here, one input of the receiver 412 is connected to the capacitor side node 526 while the other input of the receiver 412 is connected to ground. All other switches are open when receiving telemetry signals or switch 520 may be closed.

Figure 15:
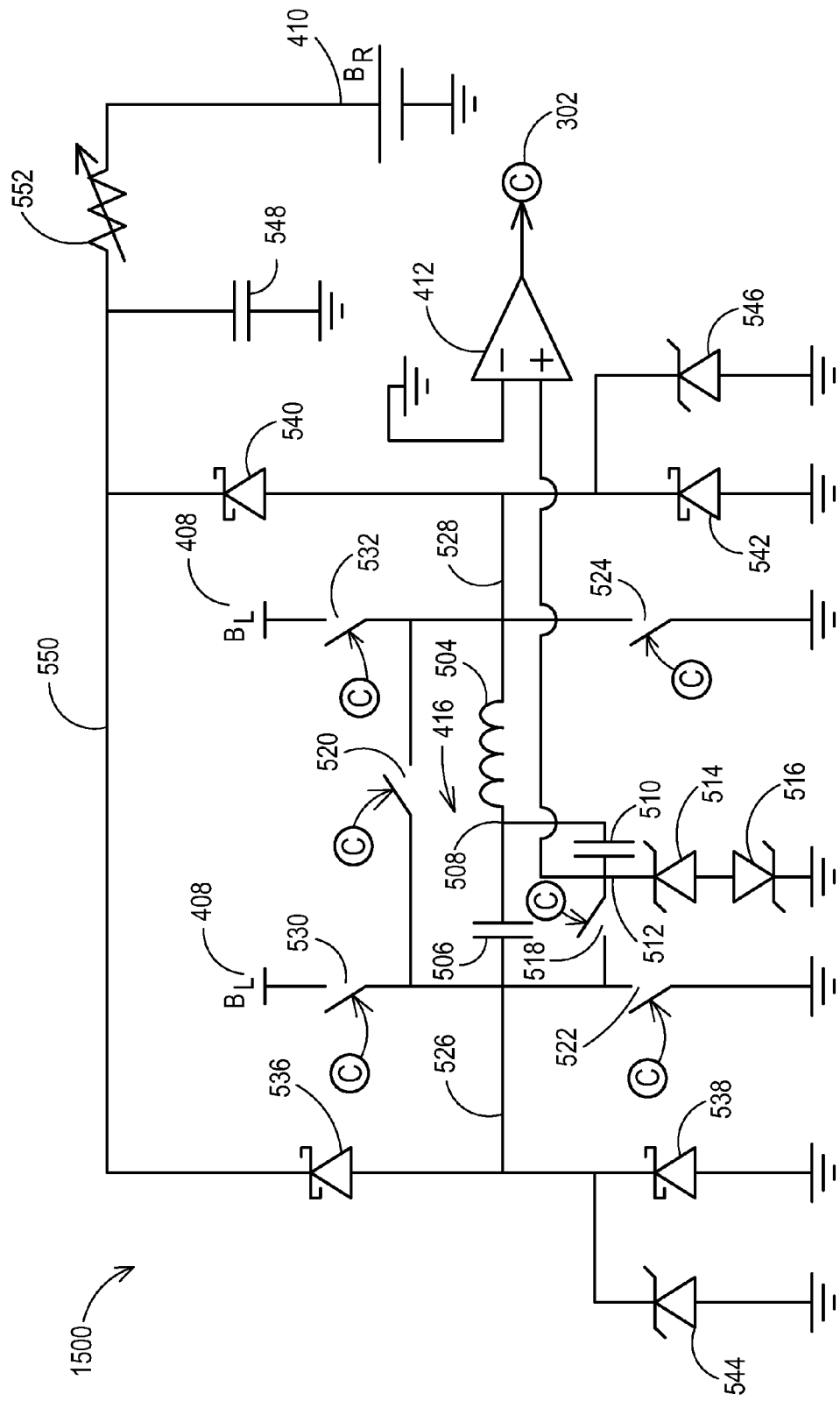
FIG. 15 shows a circuit of one example of an IMD that utilizes power management while providing for telemetry uplink and telemetry downlink at one frequency and recharge at another frequency with a single coil and with a tenth receiver configuration.

FIG. 15 shows another configuration 1500 that is the same as the configuration 500 of FIG. 5 except that the receiver's connectivity is configured differently. Here, one input of the receiver 412 is connected to the additional capacitor side node 512 so as to be capacitively coupled to the high voltage node 508 while the other input of the receiver 412 is connected to ground. All other switches are open when receiving telemetry signals or switch 520 may be closed.

Figure 16:
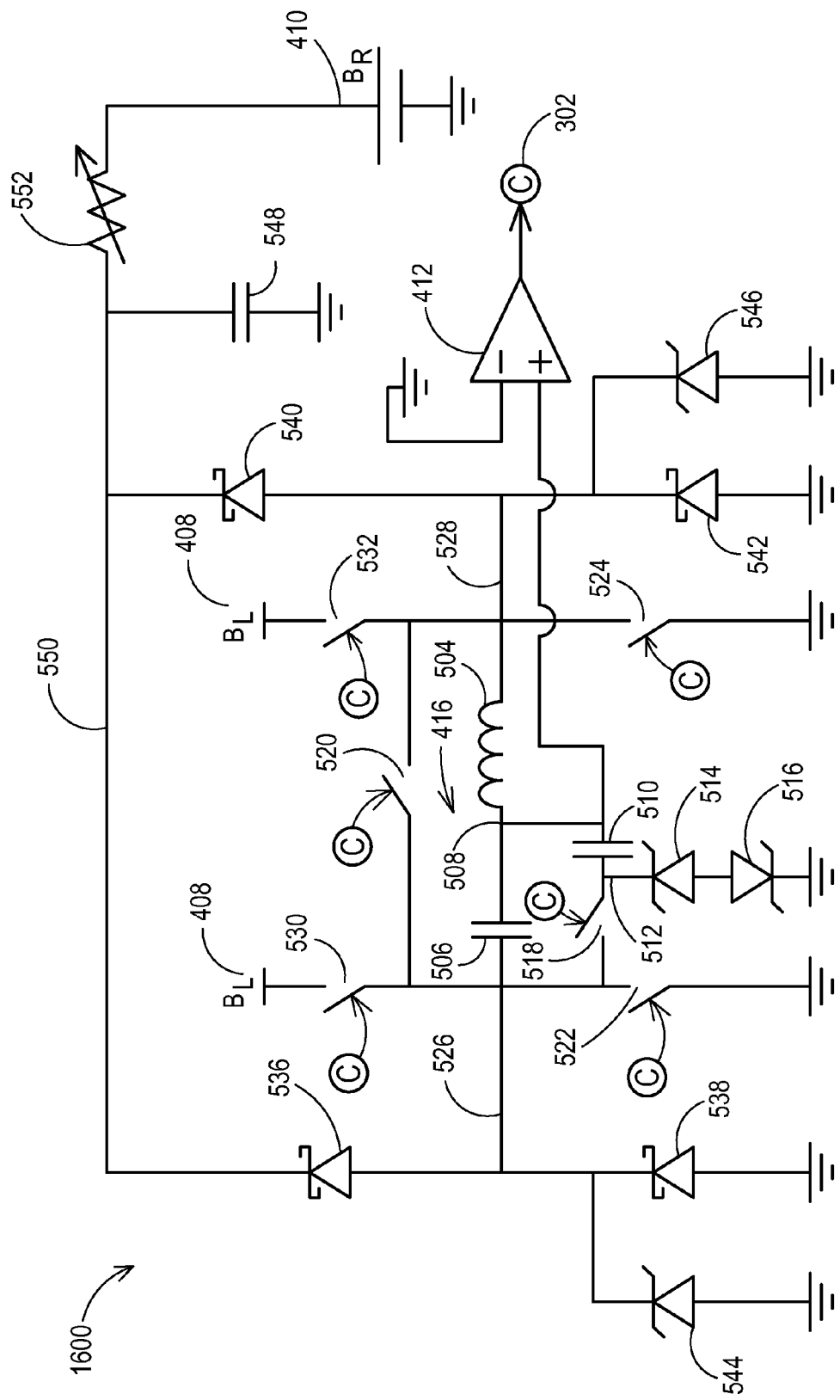
FIG. 16 shows a circuit of one example of an IMD that utilizes power management while providing for telemetry uplink and telemetry downlink at one frequency and recharge at another frequency with a single coil and with an eleventh receiver configuration.

FIG. 16 shows another configuration 1600 that is the same as the configuration 500 of FIG. 5 except that the receiver's connectivity is configured differently. Here, one input of the receiver 412 is connected directly to the high voltage node 508 while the other input of the receiver 412 is connected to ground. All other switches are open when receiving telemetry signals or switch 520 may be closed.

Figure 17:
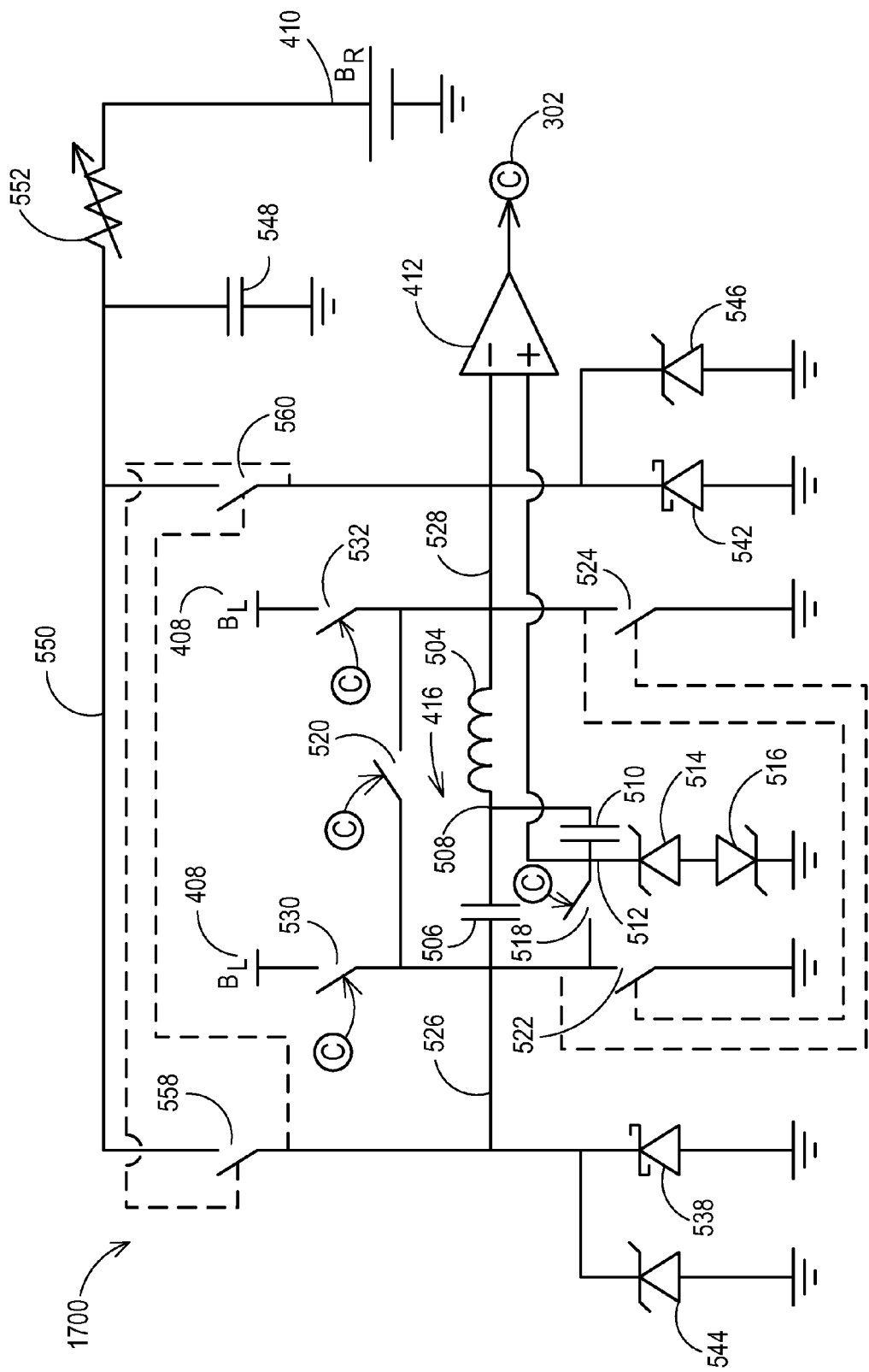
FIG. 17 shows a circuit of one example of an IMD that utilizes power management while providing for telemetry uplink and telemetry downlink at one frequency and recharge at another frequency with a single coil and with a second rectifier configuration.

FIG. 17 shows a configuration 1700 that is the same as the configuration 500 of FIG. 5 except that the rectifier is different. In this configuration 1700, the rectifier may use both high side and low side synchronous rectification by including a capacitor high side rectifier switch 558 and an inductor high side rectifier switch 560 in place of high side diodes. As discussed for the configuration of FIG. 5, the capacitor low side switch 522 and the inductor low side switch 524 may operate to provide the low side synchronous rectification.

In this particular example, the low side synchronous rectifier switches 522, 524 may be N-MOS devices while the high side synchronous rectifier switches 558, 560 may be P-MOS devices. The result based on the state machine control by the processor/controller 302 is that when the inductor side flies high, the inductor high side switch 560 and the capacitor low side switch 522 are closed while the capacitor high side switch 558 and the inductor low side switch 524 are open. When the capacitor side flies high, the capacitor high side switch 558 and the inductor low side switch 524 are closed while the inductor high side switch 560 and the capacitor low side switch are open.

The synchronous rectifier of FIG. 17 may be a pure full wave synchronous rectifier as another alternative. In that case, the diodes 538 and 542 are omitted.

While this operation of the switches 522, 524, 558, and 560 applies to recharge, during uplink and downlink telemetry operations, the capacitor low side switch 522 and the inductor low side switch 524 may operate in the same manner as discussed above in relation to FIG. 5. The capacitor high side switch 558 and the inductor high side switch 560 may remain open during uplink and downlink telemetry operations.

Figure 18:
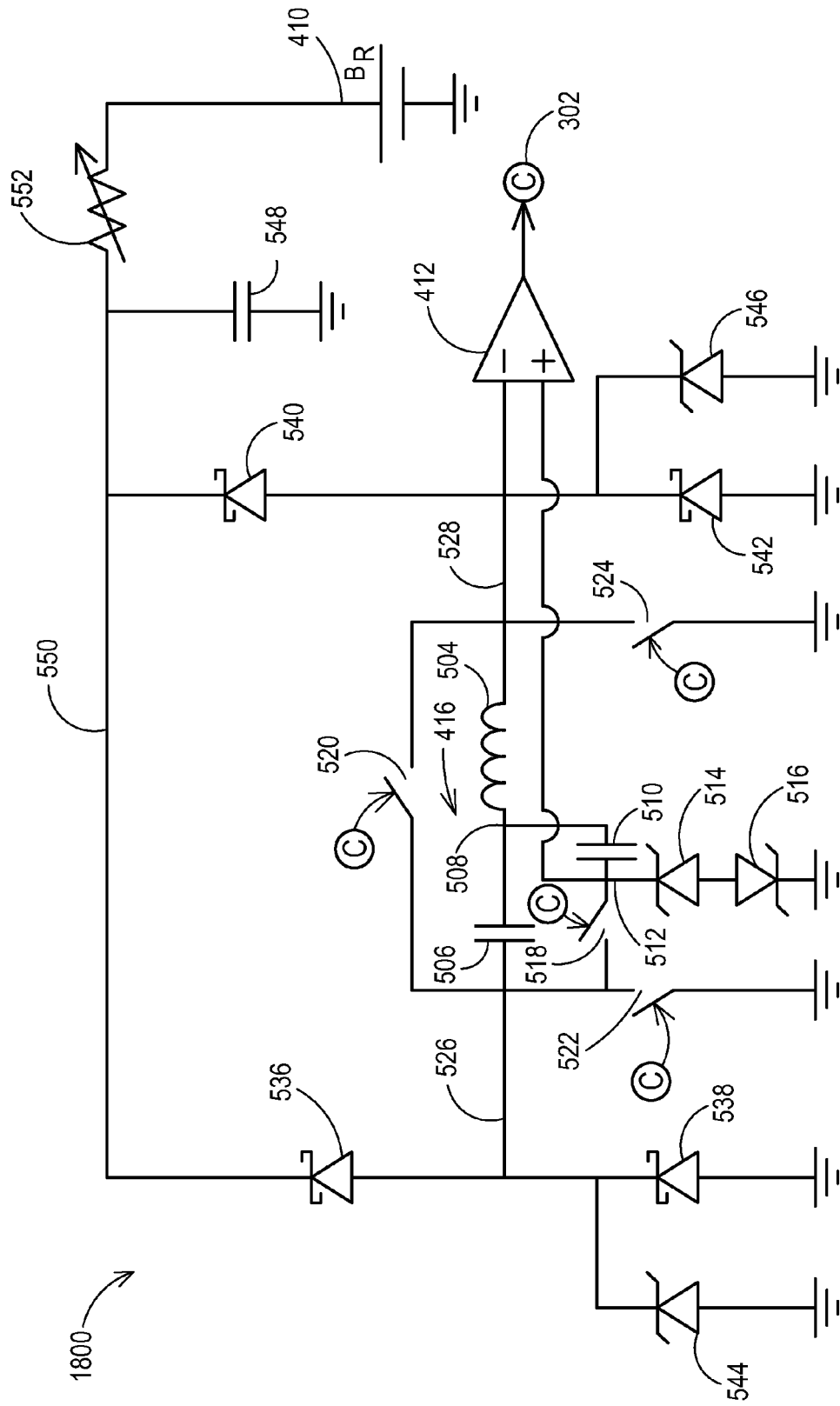
FIG. 18 shows a circuit of one example of an IMD that utilizes power management while providing for telemetry uplink at one frequency and recharge at another frequency with a single coil.
Figure 23:
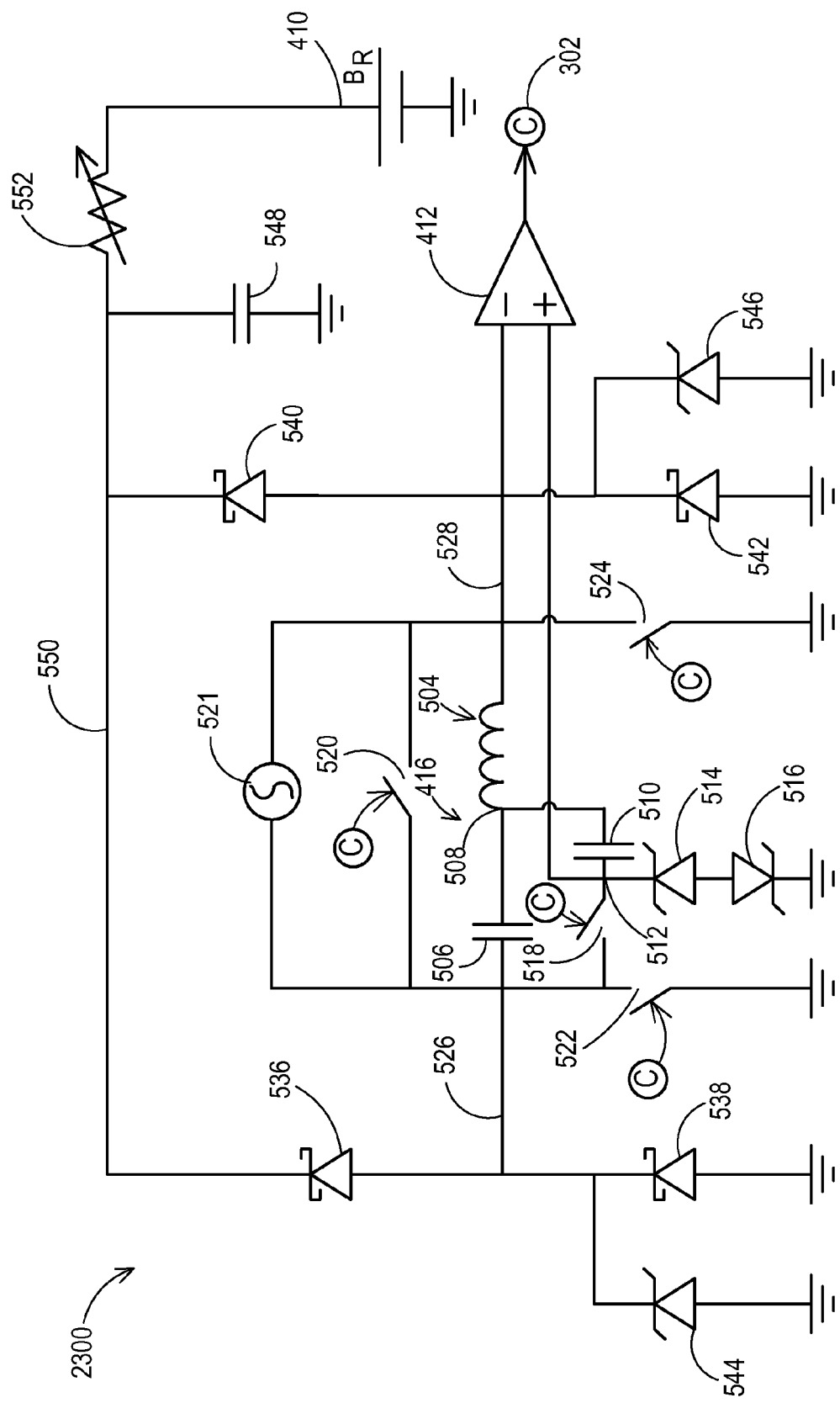
FIG. 23 shows a circuit of one example of an IMD that utilizes power management while providing for telemetry uplink and telemetry downlink at one frequency and recharge at another frequency with a single coil and with a second uplink configuration and a first rectifier configuration.
Figure 24:
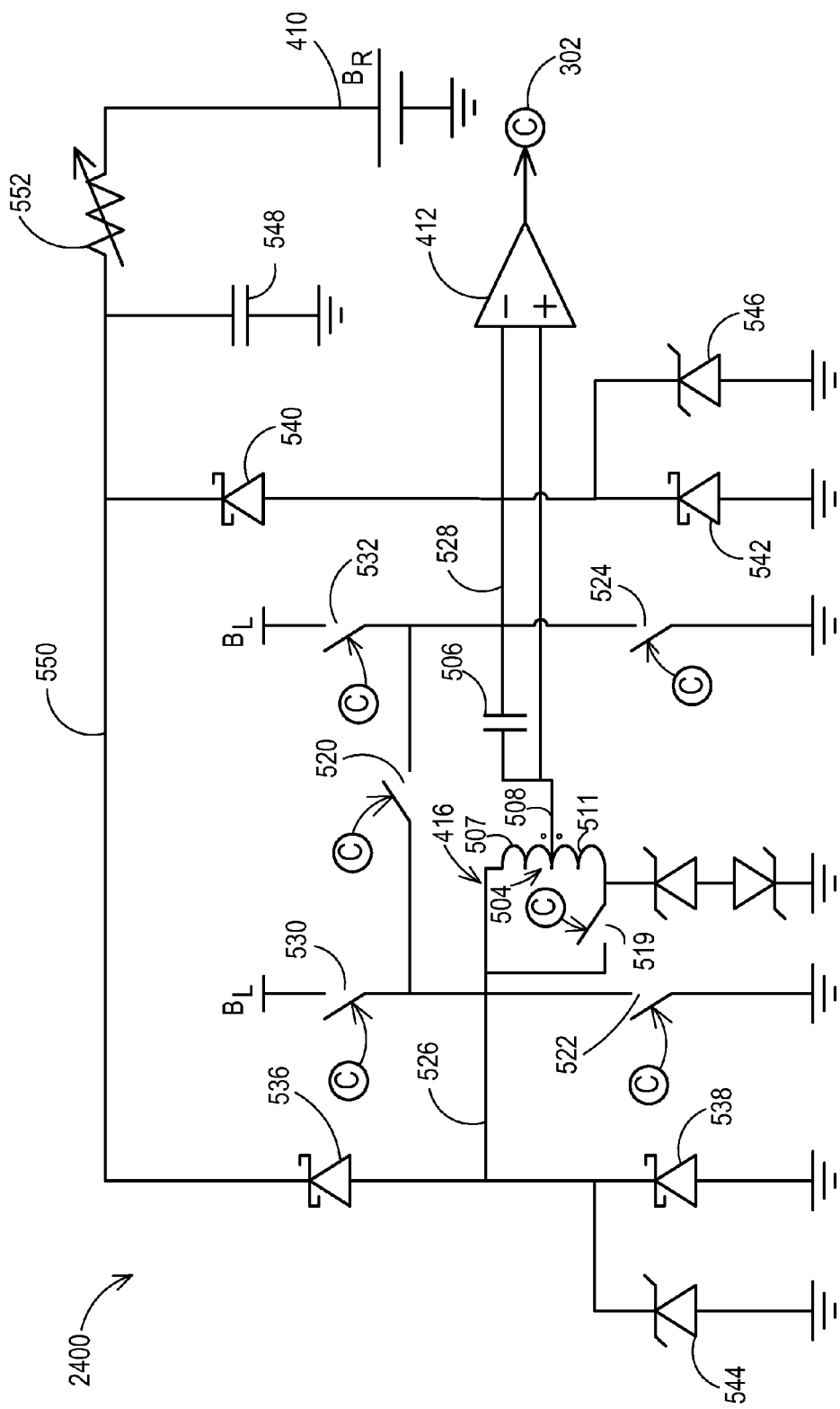
FIG. 24 shows a circuit of one example of an IMD that utilizes power management while providing for telemetry uplink and telemetry downlink at one frequency and recharge at another frequency with a single capacitor and a single coil providing variable inductance and with a first receiver configuration and a first rectifier configuration.

FIG. 18 shows another configuration 1800 like the configuration 500 of FIG. 5, except that the high side of the H-bridge created by the capacitor high side switch 530 and inductor high side switch 532 has been omitted. In this situation, the coil 504 is being used for recharge and downlink telemetry while power management features are retained. Uplink telemetry may be unnecessary in some contexts for an IMD 108. As another example, uplink telemetry may be provided at a separate frequency than downlink telemetry and may utilize a separate circuit and coil from that shown so that full-duplex communication with the external device 102 may be achieved. The variations discussed above in FIGS. 5-17 and below in FIGS. 22-24 are also applicable to the configuration 1800 to the extent those variations relate to recharging, telemetry downlink, and power management.

Figure 19:
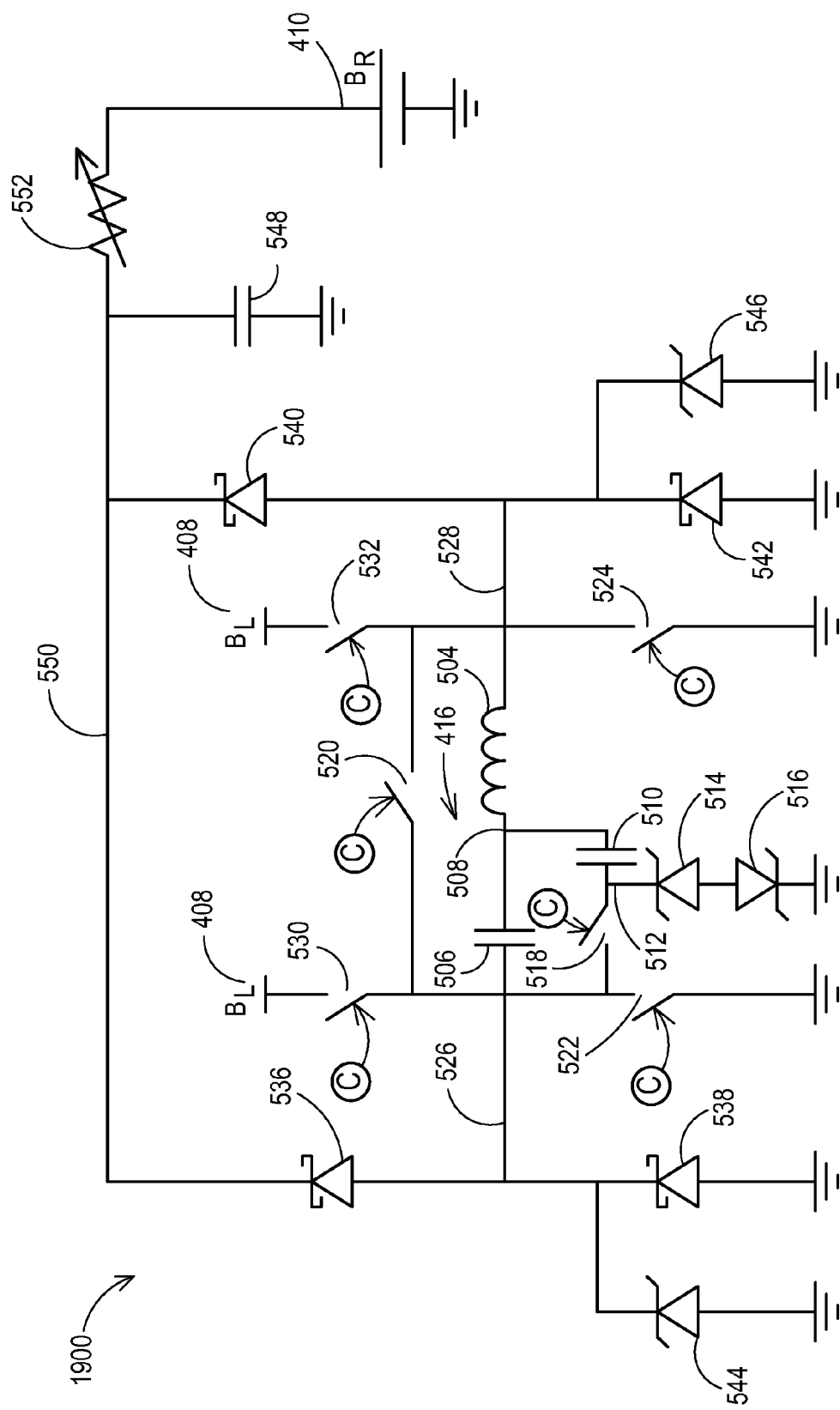
FIG. 19 shows a circuit of one example of an IMD that utilizes power management while providing for telemetry downlink at one frequency and recharge at another frequency with a single coil.

FIG. 19 shows another configuration 1900 like the configuration 500 of FIG. 5, except that the receiver 412 has been omitted. In this situation, the coil 504 is being used for recharge and uplink telemetry while power management features are retained. Downlink telemetry may be unnecessary in some contexts for an IMD 108. As another example, downlink telemetry may be provided at a separate frequency than uplink telemetry and may utilize a separate circuit and coil from that shown so that full-duplex communication with the external device 102 may be achieved. The variations discussed above in FIGS. 5, 6, and 17 and below in FIGS. 22-24 are also applicable to the configuration 1900 to the extent those variations relate to recharging, telemetry uplink, and power management.

Figure 22:
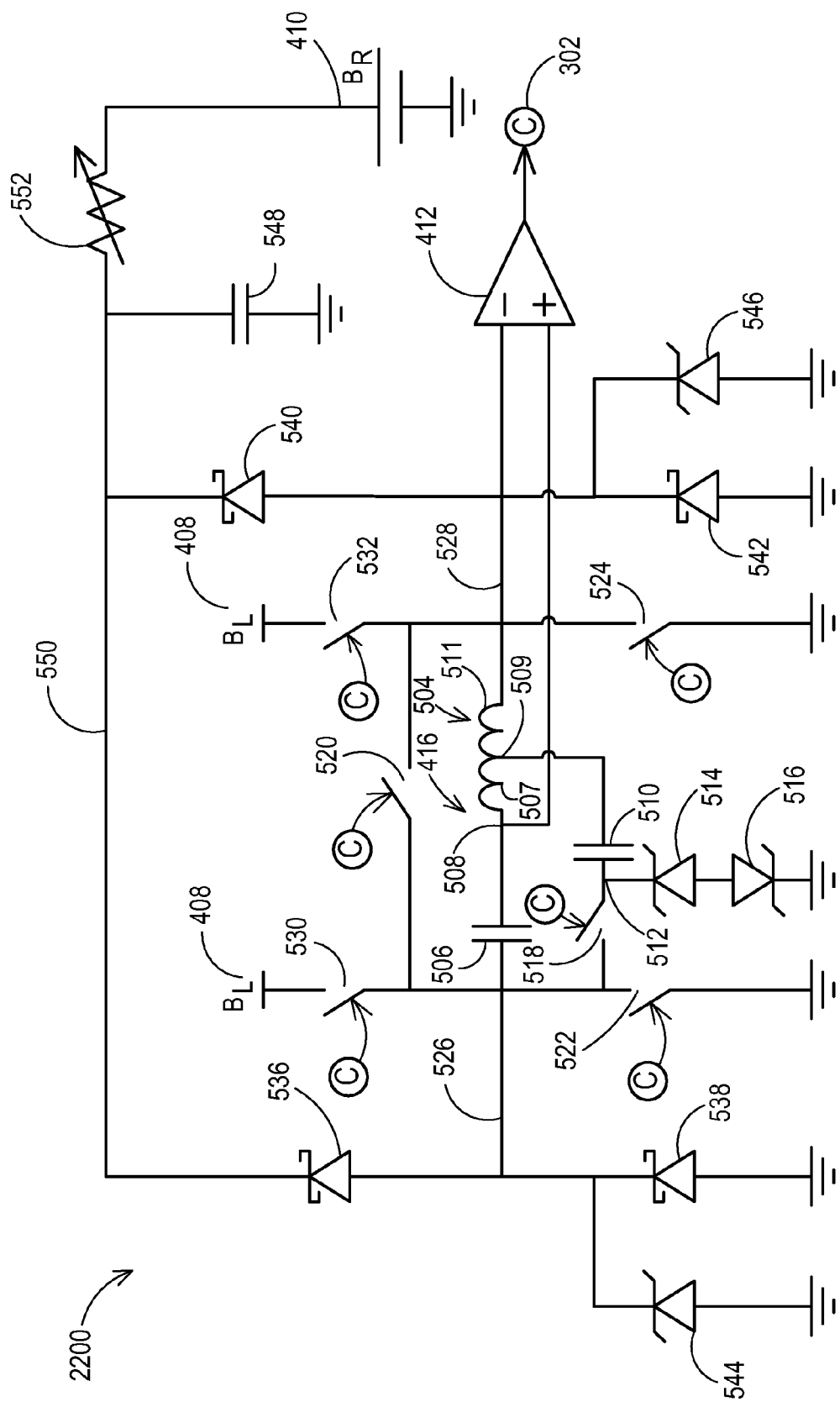
FIG. 22 shows a circuit of one example of an IMD that utilizes power management while providing for telemetry uplink and telemetry downlink at one frequency and recharge at another frequency with a single coil having a tap that provides a voltage divider and with a first receiver configuration and a first rectifier configuration.

FIG. 22 shows another configuration 2200 like the configuration 500 of FIG. 5 except that the second capacitor 510 does not connect to the high voltage node 508 while the receiver 534 is DC coupled to the high voltage node 508. Power management features are retained. In this example, the coil 504 is provided with a tap creating an intermediate node 509 and creating a first coil portion 507 and a second coil portion 509. The second capacitor 510 connects to the tap in the coil providing the intermediate node 509. A voltage divider effect is provided whereby the voltage at the intermediate node 509 which AC couples to the node 512 and tuning switch 518 is less than the voltage on the high voltage node 508. This provides additional protection to the tuning switch 518.

It will be appreciated that the selection of the capacitance for the second capacitor 510 will be different than the selection of the capacitance for the second capacitor 510 in the configuration 500 of FIG. 5 in order to tune to the same recharge frequency. It will also be appreciated that all of the variations discussed above in FIGS. 5-19 are also applicable to the example of FIG. 22, including coupling the receiver 412 to nodes besides the high voltage node 508.

FIG. 23 shows another configuration 2300 like the configuration 500 of FIG. 5 except that the transmission switches 522, 524, 530, and 532 are no longer being used to ring the coil 504. Instead, an oscillator 521 such as a sinusoidal power amplifier is connected across the tank circuit 416 to drive the tank circuit at the uplink frequency. The oscillator 521 may be activated and deactivated by the controller 302 which may also switch the oscillator 521 into and out of the circuit. Power management features are retained. The capacitor high side switch 530 and the inductor high side switch 532 may be omitted as shown. This oscillator 521 may result in fewer harmonics on the uplink carrier. It will be appreciated that all of the variations discussed above in FIGS. 5-19 and 22 are also applicable to the example of FIG. 23.

FIG. 24 shows another configuration 2400 like the configuration 500 of FIG. 5 except that the variable reactance is provided by varying the inductance rather than the capacitance. Power management features are retained. The variable inductance is achieved in this example with the single coil 504 by providing a tap on the coil 504 that establishes a first coil portion 507 and a second coil portion 509. The first coil portion is connected between the node 526 and the high voltage node 508 while the second coil portion is connected between a tuning switch 519 and the high voltage node 508. The tuning switch 519 is further connected to the node 526. A first capacitor 506 is connected between the high voltage node 508 and the node 528.

As can be seen by the dot convention of the coil 504, the first coil portion 507 and the second coil portion 509 are geometrically oriented so that their currents are directed in phase to the high voltage node 508. This may be accomplished by changing the direction of the turns of the coil of the second coil portion 509 relative to the first coil portion 507, such as where a bobbin carrying both coil portions 507, 509 is linear. As another example, this may be accomplished by maintaining the direction of the turns about the bobbin but by reversing the direction of the bobbin at the tap such as by having a U-shape.

The controller 302 operates the tuning switch 519 to switch the second coil portion 509 into and out of the tank 416. In doing so, the controller 302 is tuning the tank 416 either to the telemetry frequency or to the recharge frequency. It will be appreciated that all of the variations discussed above in FIGS. 5-19, 22 and 23 are also applicable to the example of FIG. 24.

While embodiments have been particularly shown and described, it will be understood by those skilled in the art that various other changes in the form and details may be made therein without departing from the spirit and scope of the invention.

What is claimed is:

1. An implantable medical device, comprising:
    a tank circuit comprising a variable reactance;
    a battery;
    a rectifier between the battery and the tank circuit;
    a controller in electrical communication with the variable reactance, the controller comprising logic that sets the variable reactance to a first value when receiving recharge energy and sets the variable reactance to a second value upon detecting an overcharge condition while receiving recharge energy; and
    medical circuitry in electrical communication with the battery.

2. The implantable medical device of claim 1, wherein the tank circuit comprises a coil and wherein the variable reactance comprises a variable capacitance.

3. The implantable medical device of claim 2, wherein the variable capacitance comprises:
    a first capacitor;
    a second capacitor;
    a switch that places the second capacitor in a parallel relationship with the first capacitor when in a first state, the controller being in electrical communication with the switch.

4. The implantable medical device of claim 3, wherein when the controller is not operational, the switch is in a state that sets the variable capacitance to tune the tank circuit for receiving telemetry signals, the implantable medical device further comprising at least one switch coupled to the tank circuit that the controller closes when receiving telemetry signals, the at least one switch being in the open state when the controller is not operational so that telemetry signals are received by the rectifier and provided as recharge energy to the battery.

5. The implantable medical device of claim 2, further comprising a first voltage limiter coupled directly to the coil and a second voltage limiter coupled directly to the variable capacitance.

6. The implantable medical device of claim 2, further comprising a capacitor low side switch coupled between the variable capacitance and ground and a inductor low side switch coupled between the coil and ground.

7. The implantable medical device of claim 6, wherein the controller closes the capacitor low side switch and the inductor low side switch upon detecting the overcharge condition.

8. The implantable medical device of claim 2, further comprising a circuit pathway including a switch in series with a resistor, the circuit pathway being in parallel with the coil.

9. The implantable medical device of claim 8, wherein the controller comprises logic to set the switch of the circuit pathway to a first state while the overcharge condition is undetected, and to set the switch of the circuit pathway to a second state upon detecting the overcharge condition.

10. The implantable medical device of claim 9, further comprising:
    a set of switches coupled to opposite sides of the tank circuit, and wherein the controller puts the set of switches in a first state to ring the tank circuit when detecting the overcharge condition while receiving recharge energy.

11. The implantable medical device of claim 2, further comprising a set of switches coupled to each end of the tank circuit and wherein none of the switches of the set are coupled to a node between the coil and the variable capacitance.

12. The implantable medical device of claim 1, wherein the rectifier is a full-wave rectifier.

13. The implantable medical device of claim 12, wherein the rectifier comprises a first pair of diodes allowing current flowing through the tank circuit in a first direction to be directed to the battery and a second pair of diodes allowing current flowing through the tank circuit in a second direction to be directed to the battery.

14. The implantable medical device of claim 12, wherein the rectifier comprises a first diode and a first synchronized switch allowing current flowing through the tank circuit in a first direction to be directed to the battery and a second diode and a second synchronized switch allowing current flowing through the tank circuit in a second direction to be directed to the battery.

15. The implantable medical device of claim 1, further comprising a recharge limiter in series with the battery.

16. The implantable medical device of claim 15, further comprising a filter capacitor in parallel with the recharge limiter and battery.

17. The implantable medical device of claim 1, further comprising a switch between one side of the rectifier and ground, the controller setting the switch to an open state to provide full wave rectification and setting the switch to a closed state to provide half wave rectification.

18. The implantable medical device of claim 1, wherein the tank circuit comprises a first coil portion and a second coil portion, wherein the variable reactance comprises a variable capacitance that comprises:
   a first capacitor;
   a second capacitor;
   a switch that places the second capacitor in a parallel relationship with the first capacitor when in a first state, the controller being in electrical communication with the switch, wherein a first node of the second capacitor is connected to between the first coil portion and the second coil portion and a second node of the second capacitor is connected to the switch.

19. The implantable medical device of claim 1, wherein the tank circuit comprises a capacitor and a variable inductance.

20. The implantable medical device of claim 19, wherein the variable inductance comprises:
   a first coil portion;
   a second coil portion; and
   a switch that places the second coil portion in a parallel relationship with the first coil portion when in a first state, the controller being in electrical communication with the switch.

21. An implantable medical device, comprising:
   a tank circuit comprising a variable reactance;
   a battery;
   a rectifier between the battery and the tank circuit;
   a controller in electrical communication with the variable reactance, the controller comprising logic to set the variable reactance to a first value when receiving recharge energy and to set the variable reactance to a second value upon detecting an overcharge condition while receiving recharge energy; and
medical circuitry in electrical communication with the battery,
wherein the tank circuit comprises a first coil portion and a second coil portion,
wherein the variable reactance comprises a variable capacitance that comprises:
   a first capacitor;
   a second capacitor; and
   a switch that places the second capacitor in a parallel relationship with the first capacitor when in a first state, the controller being in electrical communication with the switch, wherein a first node of the second capacitor is connected between the first coil portion and the second coil portion and a second node of the second capacitor is connected to the switch.

22. An implantable medical device, comprising:
a tank circuit comprising a variable reactance;
a battery;
a rectifier between the battery and the tank circuit;
a controller in electrical communication with the variable reactance, the controller comprising logic to set the variable reactance to a first value when receiving recharge energy and to set the variable reactance to a second value upon detecting an overcharge condition while receiving recharge energy; and
medical circuitry in electrical communication with the battery,
wherein the tank circuit comprises a capacitor and a variable inductance, wherein the variable inductance comprises:
   a first coil portion;
   a second coil portion; and
   a switch that places the second coil portion in a parallel relationship with the first coil portion when in a first state, the controller being in electrical communication with the switch.

\* \* \* \* \*